US012808853B2

(12) United States Patent
Chun et al.

(10) Patent No.: US 12,808,853 B2
(45) Date of Patent: Nov. 24, 2026

(54) METHOD FOR DIRECTLY DETECTING PATHOGENIC STRAIN HAVING RESISTANCE TO BETA-LACTAM ANTIBIOTICS

(71) Applicant: SEEGENE MEDICAL FOUNDATION, Seoul (KR)

(72) Inventors: Jong Kee Chun, Seoul (KR); Je Hyun Baek, Seoul (KR); Won Suk Yang, Gyeonggi-do (KR); Saeyoung Lee, Gyeonggi-do (KR)

(73) Assignee: Seegene Medical Foundation, Seoul (KR)

( * ) Notice: Subject to any disclaimer, the term of this patent is extended or adjusted under 35 U.S.C. 154(b) by 1054 days.

(21) Appl. No.: 17/632,110

(22) PCT Filed: Aug. 3, 2020

(86) PCT No.: PCT/KR2020/010228
§ 371 (c)(1),
(2) Date: Feb. 1, 2022

(87) PCT Pub. No.: WO2021/025413
PCT Pub. Date: Feb. 11, 2021

(65) Prior Publication Data

US 2022/0276211 A1 Sep. 1, 2022

(30) Foreign Application Priority Data

Aug. 2, 2019 (KR) ........................ 10-2019-0094321

(51) Int. Cl.
*G01N 30/88* (2006.01)
*B01D 15/36* (2006.01)
*C12N 9/86* (2006.01)
*G01N 30/96* (2006.01)
*G01N 33/68* (2006.01)

(52) U.S. Cl.
CPC ........... *G01N 30/88* (2013.01); *B01D 15/363* (2013.01); *G01N 30/96* (2013.01); *G01N 33/6848* (2013.01); *G01N 2030/8831* (2013.01); *G01N 2333/986* (2013.01)

(58) Field of Classification Search
None
See application file for complete search history.

(56) References Cited

U.S. PATENT DOCUMENTS

2012/0196309 A1 8/2012 Peaper
2013/0244230 A1 9/2013 Luider
2017/0205426 A1 7/2017 Stephenson, Jr.

FOREIGN PATENT DOCUMENTS

EP 2 816 357 A1 12/2014
KR 10-2016-0091602 A 8/2016
WO 2019034437 A1 2/2019

OTHER PUBLICATIONS

Figuero-Espinosa et al (Journal of Microbiological Methods, Apr. 2019, 159:120-127).*
Bethel et al (Antimicrobial Agents and Chemotherapy, 2011, 55:3465-3475).*
Shapiro et al (ACS Infections Diseases, 2017, 3:833-844).*
Ourghanlian et al (Antimicrobial Agents and Chemotherapy, 2017, 61:e02510-16, internet pp. 1-10).*
Spakman, D (2014. “The use of MALDI-TOF MS for the detection of β-lactamase activity in Gram-negative anerobic bacteria”. Bachelor’s Thesis, Biology. University of Groningen, Groningen, The Netherlands).*
Olsson et al (1976, Antimicrobial Agents and Chemotherapy, 9:727-735).*
Yano et al (Chinese Journal of Oceanology and Limnology).*
Hrabak et al (Journal of Clinical Microbiology, 2012, 50:2441-2443).*
Zhang et al (Anal. Chem. 2002, 74:1729-1736).*
Tanner et al (BMC Research Notes,2017, 10:48, internet pp. 1-8).*
Bush et al (Antimicrobial Agents and Chemotherapy, 2010, 54:969-976).*
Rana et al (Comparative Immunology, Microbiology and Infectious Diseases, 2022, 86: 101815, internet pp. 1-11).*
Dortet (1) (Journal of Clinical Microbiology, 2014, 52:2359-2364).*
Dortet (2) (Journal of Medical Microbiology, 2014, 63:772-776).*
Literacka et al (Eur. J. Microbiol. Infect. Dis., 2017, 36:2281-2287).*
Cheon et al , Proteomics Clinical Applications, 2021, 15:2100044, internet pp. 1-9.*
Cheon et al, Supporting Material from Proteomics Clinical Applications, 2021, 15:2100044, internet pp. 1-9.*
Cheon et a (Proteomics Clinical Applications, 2021, 15:2100044; 9 pages).*
Lee et al (Journal of Clinical Microbiology, 2022, 60: p. 1-9).*
M. Tadros et al., “Rapid detection of resistance to carbapenems and cephalosporins in Enterobacteriaceae using liquid chromatography tandem mass spectrometry,” PLoS One 13(11):e0206842 (2018).

(Continued)

*Primary Examiner* — Laura B Goddard
(74) *Attorney, Agent, or Firm* — McDonnell Boehnen Hulbert & Berghoff LLP

(57) ABSTRACT

The present invention relates to a method for detecting a pathogenic strain having resistance to β-lactam antibiotics in a biological sample, and a method for identifying a protein involved in resistance in β-lactam antibiotics, which is contained in a biological sample. According to the present invention, it is possible to quickly and accurately determine not only whether a pathogenic strain has resistance to antibiotics, but also the type of protein involved in the resistance, by directly identifying an extended spectrum β-lactamase (ESBL) protein with a truncated N-terminus through mass spectrometry. Accordingly, the present invention can be effectively utilized to quickly establish an appropriate antibiotic administration strategy at the initial stage of infection.

4 Claims, 15 Drawing Sheets

Specification includes a Sequence Listing.

(56) References Cited

OTHER PUBLICATIONS

English Translation of International Search Report, International Patent Application No. PCT/KR2020/010228, dated Nov. 16, 2020.
D.H. Cehon et al., "Optimization of a lysis method to isolate periplasmic proteins from Gram-negative bacteria for clinical mass spectrometry," Proteomics Clinical Applications, 2021, 2100044, 9 pages with 13 pages of Supplemental Information (2021).
D. Koshland et al., "Secretion of beta-lactamase requres the carboxy end of the protein," Cell, 20(3), 749-60 (1980).
M. Perilli et al., "Overexpression system and biochemical profile of CTX-M-3 extended-spectrum beta-lactamase expressed in *Escherichia coli*," FEMS Microbiology Letters, 241(2), 229-32 (2004).
S.T. Cahill et al., "Cyclic Boronates Inhibit All Classes of [beta]-lactamases," Antimicrobial Agents and Chemotherapy, 61(4), 13 pages (2017).

* cited by examiner

| Position | Sequence | AAs Before | AAs After | Oxidation | #Validated PSMs | #PSMs | Confidence [%] |
|---|---|---|---|---|---|---|---|
| 29 | QTADVQQKLAELER | YA | QS | | 1 | 2 | 100.0 |
| 43 | QSGGRLGVALINTADNSQILYR | ER | AD | | 1 | 1 | 100.0 |
| 47 | RLGVALINTADNSQILYR | GG | AD | | 1 | 1 | 100.0 |
| 48 | LGVALINTADNSQILYR | GR | AD | | 5 | 7 | 100.0 |
| 50 | VALINTADNSQILYR | LG | AD | | 1 | 1 | 100.0 |
| 53 | INTADNSQILYR | AL | AD | | 1 | 1 | 100.0 |
| 54 | NTADNSQILYR | LI | AD | | 1 | 1 | 98.3 |
| 55 | TADNSQILYR | IN | AD | | 2 | 2 | 99.6 |
| 65 | ADERFAMCSTSK | YR | VM | | 2 | 2 | 100.0 |
| 65 | ADERFAMCSTSK | YR | VM | M (7) | 2 | 3 | 100.0 |
| 66 | DERFAMCSTSK | RA | VM | M (6) | 1 | 1 | 100.0 |
| 69 | FAMCSTSK | ER | VM | M (3) | 4 | 9 | 99.6 |
| 69 | FAMCSTSKVMAVAAVLKK | ER | SE | M (10, 3) | 2 | 3 | 100.0 |
| 69 | FAMCSTSK | ER | VM | | 1 | 6 | 99.5 |
| 69 | FAMCSTSKVMAVAAVLKK | ER | SE | M (3) | 1 | 2 | 100.0 |
| 69 | FAMCSTSKVMAVAAVLKK | ER | SE | M (10) | 3 | 3 | 100.0 |
| 77 | VMAVAAVLKK | SK | SE | | 9 | 35 | 99.8 |
| 77 | VMAVAAVLK | SK | KS | M (2) | 33 | 38 | 100.0 |
| 77 | VMAVAAVLKK | SK | SE | M (2) | 69 | 90 | 100.0 |
| 77 | VMAVAAVLKKSESEPNLLNQR | SK | VE | M (2) | 2 | 3 | 100.0 |
| 77 | VMAVAAVLK | SK | KS | | 2 | 11 | 99.6 |
| 77 | VMAVAAVLKKSESEPNLLNQR | SK | VE | | 2 | 3 | 100.0 |
| 78 | MAVAAVLK | KV | KS | M (1) | 1 | 1 | 100.0 |
| 78 | MAVAAVLKK | KV | SE | M (1) | 1 | 1 | 98.3 |
| 79 | AVAAVLKK | VM | SE | | 4 | 5 | 99.6 |
| 86 | KSESEPNLLNQRVEIK | LK | KS | | 1 | 3 | 100.0 |
| 86 | KSESEPNLLNQR | LK | VE | | 37 | 56 | 100.0 |
| 87 | SESEPNLLNQR | KK | VE | | 38 | 44 | 100.0 |
| 87 | SESEPNLLNQRVEIKK | KK | SD | | 2 | 3 | 100.0 |
| 87 | SESEPNLLNQRVEIK | KK | KS | | 2 | 2 | 100.0 |
| 89 | SEPNLLNQR | SE | VE | | 1 | 1 | 98.3 |
| 98 | VEIKKSDLVNYNPIAEK | QR | HV | | 2 | 3 | 100.0 |
| 101 | KKSDLVNYNPIAEK | EI | HV | | 1 | 2 | 100.0 |
| 102 | KSDLVNYNPIAEK | IK | HV | | 45 | 68 | 100.0 |
| 103 | SDLVNYNPIAEK | KK | HV | | 24 | 34 | 100.0 |
| 105 | LVNYNPIAEK | SD | HV | | 2 | 2 | 99.5 |
| 115 | HVDGTMSLAELSAAALQYSDNVAMNK | EK | LI | M (24, 6) | 1 | 1 | 100.0 |
| 115 | HVDGTMSLAELSAAAL | EK | QY | M (6) | 1 | 1 | 98.3 |
| 128 | AALQYSDNVAMNK | SA | LI | M (11) | 1 | 1 | 100.0 |
| 129 | ALQYSDNVAMNK | AA | LI | M (10) | 1 | 1 | 100.0 |
| 129 | ALQYSDNVAMNK | AA | LI | | 1 | 1 | 100.0 |
| 140 | KLISHVGGPASVTAFAR | MN | QL | | 1 | 1 | 100.0 |
| 141 | LISHVGGPASVTAF | NK | AR | | 2 | 3 | 99.6 |
| 141 | LISHVGGPASVTAFAR | NK | QL | | 59 | 64 | 100.0 |
| 142 | ISHVGGPASVTAFAR | KL | QL | | 1 | 2 | 100.0 |
| 143 | SHVGGPASVTAFAR | LI | QL | | 2 | 2 | 100.0 |
| 156 | RQLGDETFR | FA | LD | | 3 | 3 | 99.5 |
| 157 | QLGDETFRLDR | AR | TE | | 1 | 5 | 96.5 |
| 157 | QLGDETFR | AR | LD | | 27 | 42 | 99.8 |
| 165 | LDRTEPTLNTAIPGDPRD | FR | TT | | 2 | 2 | 99.6 |
| 165 | LDRTEPTLNTAIPGDPR | FR | DT | | 42 | 61 | 100.0 |
| 165 | LDRTEPTLNTAIPGDPRDTTSPR | FR | AM | | 4 | 7 | 100.0 |
| 167 | RTEPTLNTAIPGDPR | LD | DT | | 2 | 2 | 99.6 |
| 168 | TEPTLNTAIPGDPRD | DR | TT | | 1 | 1 | 98.3 |
| 168 | TEPTLNTAIPGDPR | DR | DT | | 25 | 30 | 100.0 |
| 168 | TEPTLNTAIPGDPRDTTSPR | DR | AM | | 3 | 4 | 100.0 |
| 170 | PTLNTAIPGDPR | TE | DT | | 1 | 1 | 100.0 |
| 188 | AMAQTLRNLTLGK | PR | AL | M (2) | 1 | 2 | 98.3 |
| 195 | NLTLGKALGDSQR | LR | AQ | | 1 | 1 | 100.0 |
| 208 | AQLVTWMK | QR | GN | | 3 | 10 | 99.6 |
| 208 | AQLVTWMK | QR | GN | M (7) | 27 | 31 | 100.0 |
| 216 | GNTTGAASIQAGLPASWVVGDK | MK | TG | | 6 | 8 | 100.0 |
| 221 | AASIQAGLPASWVVGDK | TG | TG | | 1 | 1 | 100.0 |
| 222 | ASIQAGLPASWVVGDK | GA | TG | | 1 | 1 | 100.0 |
| 223 | SIQAGLPASWVVGDK | AA | TG | | 1 | 1 | 100.0 |
| 224 | IQAGLPASWVVGDK | AS | TG | | 1 | 2 | 100.0 |
| 238 | TGSGDYGTTNDIAVIWPKDR | DK | AP | | 1 | 1 | 100.0 |
| 238 | TGSGDYGTTNDIAVIWPK | DK | DR | | 7 | 7 | 100.0 |
| 240 | SGDYGTTNDIAVIWPK | TG | DR | | 1 | 1 | 100.0 |
| 243 | YGTTNDIAVIWPK | GD | DR | | 1 | 1 | 100.0 |
| 244 | GTTNDIAVIWPK | DY | DR | | 1 | 1 | 100.0 |
| 245 | TTNDIAVIWPK | YG | DR | | 1 | 1 | 98.3 |
| 248 | DIAVIWPK | TN | DR | | 1 | 2 | 98.3 |
| 254 | PKDRAPLILVTYFTQPQPK | IW | AE | | 1 | 1 | 100.0 |
| 256 | DRAPLILVTYFTQPQPK | PK | AE | | 33 | 34 | 100.0 |
| 256 | DRAPLILVTYFTQPQPKAESR | PK | RD | | 3 | 3 | 100.0 |
| 257 | RAPLILVTYFTQPQPK | KD | AE | | 2 | 2 | 100.0 |
| 258 | APLILVTYFTQPQPK | DR | AE | | 13 | 16 | 100.0 |
| 261 | ILVTYFTQPQPK | PL | AE | | 4 | 6 | 100.0 |
| 263 | VTYFTQPQPK | IL | AE | | 2 | 2 | 99.5 |
| 273 | AESRRDVLASAAK | PK | IV | | 2 | 3 | 99.6 |
| 277 | RDVLASAAKIVTNGL | SR | - | | 1 | 1 | 98.3 |

FIG. 5A

CTX-M1 MVKKSLRQFTLMATATVTLLLGSVPLYAQTADVQQKLAELERQSGGRLGVALINTADNSQ
CTX-M14 MVTKRVQRMMFAAAACIPLLLGSAPLYAQTSAVQQKLAALEKSSGGRLGVALIDTADNTQ
CTX-M15 MVKKSLRQFTLMATATVTLLLGSVPLYAQTADVQQKLAELERQSGGRLGVALINTADNSQ
CTX-M27 MVTKRVQRMMFAAAACIPLLLGSAPLYAQTSAVQQKLAALEKSSGGRLGVALIDTADNTQ
CTX-M142 MVKKSLRQFTLMATATVTLLLGSVPLYAQTANVQQKLAELERQSGGRLGVALINTADNSQ
CTX-M186 MVKKSLRQFTLMATATVTLSLGSVPLYAQTADVQQKLAELERQSGGRLGVALINTADNSQ

CTX-M1 ILYRADERFAMCSTSKVMAVAAVLKKSESEPNLLNQRVEIKKSDLVNYNPIAEKHVDGTM
CTX-M14 VLYRGDERFPMCSTSKVMAAAAVLKQSETQKQLLNQPVEIKPADLVNYNPIAEKHVNGTM
CTX-M15 ILYRADERFAMCSTSKVMAAAAVLKKSESEPNLLNQRVEIKKSDLVNYNPIAEKHVNGTM
CTX-M27 VLYRGDERFPMCSTSKVMAAAAVLKQSETQKQLLNQPVEIKPADLVNYNPIAEKHVNGTM
CTX-M142 ILYRADERFAMCSTSKVMAAAAVLKKSESEPNLLNQRVEIKKSDLVNYNPIAEKHVNGTM
CTX-M186 ILYRADERFAMCSTSKVMAAAAVLKKSESEPNLLNQRVEIKKSDLVNYNPIAEKHVNGTM

CTX-M1 SLAELSAAALQYSDNVAMNKLISHVGGPASVTAFARQLGDETFRLDRTEPTLNTAIPGDP
CTX-M14 TLAELSAAALQYSDNTAMNKLIAQLGGPGGVTAFARAIGDETFRLDRTEPTLNTAIPGDP
CTX-M15 SLAELSAAALQYSDNVAMNKLIAHVGGPASVTAFARQLGDETFRLDRTEPTLNTAIPGDP
CTX-M27 TLAELSAAALQYSDNTAMNKLIAQLGGPGGVTAFARAIGDETFRLDRTEPTLNTAIPGDP
CTX-M142 SLAELSAAALQYSDNVAMNKLIAHVGGPASVTAFARQLGDETFRLDRTEPTLNTAIPGDP
CTX-M186 SLAELSAAALQYSDNVAMNKLIAHVGGPASVTAFARQLGDETFRLDRTEPTLNTAIPGDP

CTX-M1 RDTTSPRAMAQTLRNLTLGKALGDSQRAQLVTWMKGNTTGAASIQAGLPASWVVGDKTGS
CTX-M14 RDTTTPRAMAQTLRQLTLGHALGETQRAQLVTWLKGNTTGAASIRAGLPTSWTVGDKTGS
CTX-M15 RDTTSPRAMAQTLRNLTLGKALGDSQRAQLVTWMKGNTTGAASIQAGLPASWVVGDKTGS
CTX-M27 RDTTTPRAMAQTLRQLTLGHALGETQRAQLVTWLKGNTTGAASIRAGLPTSWTVGDKTGS
CTX-M142 RDTTSPRAMAQTLRNLTLGKALGDSQRAQLVTWMKGNTTGAASIQAGLPASWVVGDKTGS
CTX-M186 RDTTSPRAMAQTLRNLTLGKALGDSQRAQLVTWMKGNTTGAASIQAGLPASWVVGDKTGS

CTX-M1 GDYGTTNDIAVIWPKDRAPLILVTYFTQPQPKAESRRDVLASAAKIVTNGL
CTX-M14 GDYGTTNDIAVIWPQGRAPLVLVTYFTQPQQNAESRRDVLASAARIIAEGL
CTX-M15 GGYGTTNDIAVIWPKDRAPLILVTYFTQPQPKAESRRDVLASAAKIVTDGL
CTX-M27 GGYGTTNDIAVIWPQGRAPLVLVTYFTQPQQNAESRRDVLASAARIIAEGL
CTX-M142 GGYGTTNDIAVIWPKDRAPLILVTYFTQPQPKAESRRDVLASAAKIVTDGL
CTX-M186 GGYGTTNDIAVIWPKDRAPLILVTYFTQPQPKAESRRDVLASAAKIVTDGL

M = oxidation sites

FIG. 5B

SEQUENCE LISTING

```
<160> NUMBER OF SEQ ID NOS: 4

<210> SEQ ID NO 1
<211> LENGTH: 876
<212> TYPE: DNA
<213> ORGANISM: Escherichia coli

<400> SEQUENCE: 1

atggttaaaa aatcactgcg tcagttcacg ctgatggcga cggcaaccgt cacgctgttg      60

ttaggaagtg tgccgctgta tgcgcaaacg gcggacgtac agcaaaaact tgccgaatta     120

gagcggcagt cgggaggaag actgggtgtg gcattgatta acacagcaga taattcgcaa     180
```

```
atactttatc gtgctgatga gcgctttgcg atgtgcagca ccagtaaagt gatggccgtg    240

gccgcggtgc tgaagaaaag tgaaagcgaa ccgaatctgt taaatcagcg agttgagatc    300

aaaaaatctg acttggttaa ctataatccg attgcggaaa agcacgtcga tgggacgatg    360

tcactggctg agcttagcgc ggccgcgcta cagtacagcg ataacgtggc gatgaataag    420

ctgatttctc acgttggcgg cccggctagc gtcaccgcgt tcgcccgaca gctgggagac    480

gaaacgttcc gtctcgaccg taccgagccg acgttaaaca ccgccattcc gggcgatccg    540

cgtgatacca cttcacctcg ggcaatggcg caaactctgc gtaatctgac gctgggtaaa    600

gcattgggtg acagccaacg ggcgcagctg gtgacatgga tgaaaggcaa taccaccggt    660

gcagcgagca ttcaggctgg actgcctgct tcctgggttg tgggggataa aaccggcagc    720

ggtgactatg gcaccaccaa cgatatcgcg gtgatctggc caaaagatcg tgcgccgctg    780

attctggtca cttacttcac ccagcctcaa cctaaggcag aaagccgtcg cgatgtatta    840

gcgtcggcgg ctaaaatcgt caccaacggt ttgtga                              876


<210> SEQ ID NO 2
<211> LENGTH: 291
<212> TYPE: PRT
<213> ORGANISM: Escherichia coli

<400> SEQUENCE: 2

Met Val Lys Lys Ser Leu Arg Gln Phe Thr Leu Met Ala Thr Ala Thr
1               5                   10                  15

Val Thr Leu Leu Leu Gly Ser Val Pro Leu Tyr Ala Gln Thr Ala Asp
            20                  25                  30

Val Gln Gln Lys Leu Ala Glu Leu Glu Arg Gln Ser Gly Gly Arg Leu
        35                  40                  45

Gly Val Ala Leu Ile Asn Thr Ala Asp Asn Ser Gln Ile Leu Tyr Arg
    50                  55                  60

Ala Asp Glu Arg Phe Ala Met Cys Ser Thr Ser Lys Val Met Ala Val
65                  70                  75                  80

Ala Ala Val Leu Lys Lys Ser Glu Ser Glu Pro Asn Leu Leu Asn Gln
                85                  90                  95

Arg Val Glu Ile Lys Lys Ser Asp Leu Val Asn Tyr Asn Pro Ile Ala
            100                 105                 110

Glu Lys His Val Asp Gly Thr Met Ser Leu Ala Glu Leu Ser Ala Ala
        115                 120                 125

Ala Leu Gln Tyr Ser Asp Asn Val Ala Met Asn Lys Leu Ile Ser His
    130                 135                 140

Val Gly Gly Pro Ala Ser Val Thr Ala Phe Ala Arg Gln Leu Gly Asp
145                 150                 155                 160

Glu Thr Phe Arg Leu Asp Arg Thr Glu Pro Thr Leu Asn Thr Ala Ile
                165                 170                 175

Pro Gly Asp Pro Arg Asp Thr Thr Ser Pro Arg Ala Met Ala Gln Thr
            180                 185                 190

Leu Arg Asn Leu Thr Leu Gly Lys Ala Leu Gly Asp Ser Gln Arg Ala
        195                 200                 205

Gln Leu Val Thr Trp Met Lys Gly Asn Thr Thr Gly Ala Ala Ser Ile
    210                 215                 220

Gln Ala Gly Leu Pro Ala Ser Trp Val Val Gly Asp Lys Thr Gly Ser
225                 230                 235                 240

Gly Asp Tyr Gly Thr Thr Asn Asp Ile Ala Val Ile Trp Pro Lys Asp
                245                 250                 255
```

-continued

```
Arg Ala Pro Leu Ile Leu Val Thr Tyr Phe Thr Gln Pro Gln Pro Lys
            260                 265                 270

Ala Glu Ser Arg Arg Asp Val Leu Ala Ser Ala Ala Lys Ile Val Thr
        275                 280                 285

Asn Gly Leu
    290


<210> SEQ ID NO 3
<211> LENGTH: 33
<212> TYPE: DNA
<213> ORGANISM: Artificial Sequence
<220> FEATURE:
<223> OTHER INFORMATION: CTX-M primer 1

<400> SEQUENCE: 3

aactgcagga tggttaaaaa atcactgcgt cag                                   33


<210> SEQ ID NO 4
<211> LENGTH: 29
<212> TYPE: DNA
<213> ORGANISM: Artificial Sequence
<220> FEATURE:
<223> OTHER INFORMATION: CTX-M primer 2

<400> SEQUENCE: 4

ggaattctca caaaccgttg gtgacgatt                                        29
```

METHOD FOR DIRECTLY DETECTING PATHOGENIC STRAIN HAVING RESISTANCE TO BETA-LACTAM ANTIBIOTICS

CROSS-REFERENCE TO RELATED APPLICATIONS

This application is a U.S. National Stage entry of International Patent Application no. PCT/KR2020/010228, filed Aug. 3, 2020, which claims the benefit of priority of Korean Patent Application no. 10-2019-0094321, filed Aug. 29, 2019.

SEQUENCE LISTING STATEMENT

This application includes an electronically submitted Sequence Listing in text format. The text file contains a sequence listing entitled "22-0111-WO-US_ST25.txt" created on Feb. 1, 2022 and is 5 kilobytes in size. The Sequence Listing contained in this text file is part of the specification and is hereby incorporated by reference herein in its entirety.

TECHNICAL FIELD

The present invention relates to a method of directly detecting a protein involved in resistance to beta-lactam antibiotics by top-down mass spectrometry without pretreatment of a sample.

BACKGROUND ART

As the therapeutic efficacy of commercially available antibiotics has sharply decreased due to the continuous increase in antibiotic-resistant bacteria, strategies for improving the therapeutic efficacy by appropriate antibiotic administration to patients infected with pathogens and inducing reduction of antibiotic-resistant bacteria have been actively studied. Currently, Minimum Inhibitory Concentration (MIC) testing is being conducted to identify whether antibiotic resistance is present, but it takes 18 hours or more for microbial culture, which is an essential step, and has low accuracy, and hence it is impossible to achieve rapid identification and select an optimal antibiotic in the early stage of infection. Gene diagnosis techniques using real-time PCR, etc. are also limited in their application to rapid and accurate high-throughput diagnosis, because they require complicated and expensive sample pretreatment in the gene extraction and amplification process, advance information on the nucleotide sequence of the target gene is essential, and inaccurate information about antibiotic resistance is included due to detection of enzyme genes that have already lost antibiotic degradation activity.

Mass spectrometry methods, including MALDI-TOF, are low-cost and high-efficiency identification systems compared to sequencing methods based on PCR, and can be an important means for rapid identification of microorganisms. In addition, using these methods, it is possible to achieve sample treatment after strain culture and stain identification within 10 minutes, and to quickly identify a strain with the same mass value by comparing mass data for unknown strains with mass data in a database constructed through mass spectrometry data.

However, conventional mass spectrometry methods cannot accurately determine the type of antibiotic resistance protein, and are cumbersome because they involve degrading the target resistance protein into peptide fragments using a protease, and then indirectly inferring the type of resistance protein through the mass values of these fragments. In addition, these methods have many problems in terms of reliability.

Accordingly, the present inventors have attempted to develop a method capable of rapidly and accurately identifying a strain having resistance to beta-lactam antibiotics and a protein involved in the resistance by selecting proteins directly involved in resistance to beta-lactam antibiotics, measuring the exact mass values of in vivo active forms of these proteins, and then performing top-down mass spectrometry on these proteins without pretreatment such as enzyme treatment.

Through the specification, a number of publications and patent documents are referred to and cited. The disclosure of the cited publications and patent documents is incorporated herein by reference in its entirety to more clearly describe the state of the related art and the present invention.

DISCLOSURE

Technical Problem

The present inventors made intensive research efforts to develop an efficient diagnostic method for detecting beta-lactamase protein involved in resistance to beta-lactam antibiotics in a simple manner with high reliability. As a result, the present inventors have newly discovered that the extended spectrum β-lactamase (ESBL) proteins of a strain having resistance to beta-lactam antibiotics are present in active forms due to cleavage of some of N-terminal residues in vivo after infection, and have found that, when these ESBL proteins in active forms are analyzed directly by mass spectrometry, it is possible to rapidly and accurately determine not only whether a pathogenic strain has resistance to the antibiotics but also the type of protein involved in the resistance, thereby completing the present invention.

Therefore, an object of the present invention is to provide a method of detecting a pathogenic strain having resistance to beta-lactam antibiotics in a biological sample.

Another object of the present invention is to provide a method of identifying a protein involved in resistance to beta-lactam antibiotics in a biological sample.

Other objects and advantages of the present invention will become more apparent by the following detailed description of the invention, the appended claims and the accompanying drawings.

Technical Solution

One aspect of the present invention provides a method of detecting a pathogenic strain having resistance to β-lactam antibiotics in a biological sample, the method comprising steps of:

(a) isolating a protein expressed by a pathogenic strain in a biological sample isolated from a subject; and (b) performing top-down mass spectrometry on the isolated protein, wherein it is determined that the pathogenic strain having resistance to β-lactam antibiotics is present in the biological sample, when a protein having the same mass as β-lactamase from which 28 amino acid residues at the N-terminus have been removed is detected as a result of the mass spectrometry.

The present inventors made intensive research efforts to develop an efficient diagnostic method for detecting beta-lactamase protein involved in resistance to beta-lactam antibiotics in a simple manner with high reliability. As a result, the present inventors have newly discovered that the extended spectrum β-lactamase (ESBL) proteins of a strain having resistance to beta-lactam antibiotics are present in active forms due to cleavage of some of N-terminal residues in vivo after infection, and have found that, when these ESBL proteins in active forms are analyzed directly by mass spectrometry, it is possible to rapidly and accurately determine not only whether a pathogenic strain has resistance to the antibiotics but also the type of protein involved in the resistance, making it possible to establish an appropriate strategy for antibiotic administration at an early stage of infection.

As used herein, the term "pathogenic strain" refers to any bacteria that act as the cause of an infection or disease, including, for example, but not limited to, *Staphylococcus aureus, Streptococcus, Escherichia coli, Klebsiella pneumoniae, Pseudomonas aeruginosa, Pseudomonas otitidis, Micrococcus luteus, Citrobacter koseri, Proteus mirabilis*, and *Mycobacterium ulcerans*.

As used herein, the expression "having resistance to antibiotics" means that a specific pathogenic microorganism can grow even in an environment in which antibiotics against the microorganism are present at high concentration or in an effective amount. Whether the pathogenic microorganism has antibiotic resistance may be determined by detecting the presence of an enzyme protein, which is secreted by the pathogenic microorganism and removes or reduces the activities of the antibiotics by degrading the antibiotics. For example, beta-lactam antibiotics that inhibit bacterial cell wall synthesis, such as penicillin, cephalosporin, monobactam, and carbapenem, are inactivated by β-lactamase so that they cannot inhibit pathogens expressing β-lactamase. Accordingly, the term "resistance" is used interchangeably with the term "low therapeutic responsiveness".

As used herein, the term "treatment" refers to (a) inhibiting the progress of a disease, disorder or symptom; (b) alleviating a disease, disorder or symptom; or (c) eliminating a disease, disorder or symptom. Thus, the term "therapeutic responsiveness" refers to the degree to which beta-lactam antibiotics, when administered in a therapeutically effective amount to a patient infected with a pathogenic strain, act as described above in vivo.

As used herein, the term "prevention" refers to inhibiting the occurrence of a disease or disorder in a subject that has never been diagnosed as having the disease or disorder, but is likely to have the disease or disorder. Thus, "prophylactic responsiveness" refers to the degree to which beta-lactam antibiotics, when administered in a prophylactically effective amount to a normal person whose infection has not yet been confirmed, act to inhibit infection in vivo.

As used herein, the term "biological sample" refers to any samples, including, for example, but not limited to, blood, tissues, organs, cells or cell cultures, which are obtained from mammals, including humans, and contain or are likely to contain a pathogenic strain to be inhibited with beta-lactam antibiotics.

As used herein, the term "subject" refers to a subject that provides a sample for examining the presence of a pathogenic strain to be inhibited with beta-lactam antibiotics or whether the strain has resistance to the antibiotics, and ultimately refers to a subject to be analyzed for whether or not infection with the pathogenic strain having resistance to the antibiotics has occurred. Examples of the subject include, without limitation, humans, mice, rats, guinea pigs, dogs, cats, horses, cattle, pigs, monkeys, chimpanzees, baboons or rhesus monkeys, specifically humans. Since the composition of the present invention provides information for predicting not only therapeutic responsiveness but also prophylactic responsiveness to beta-lactam antibiotics, the subject of the present invention may be a patient infected with the strain or may also be a healthy subject whose infection has not yet been confirmed.

As used herein, the term "top-down mass spectrometry" refers to an analysis that directly measures the mass value of a full-length protein without performing the process of fragmenting the protein into peptide fragments, and specifically, refers to an analysis in which fragmentation of the target protein is not performed before the protein sample is injected into a mass spectrometer. Another feature of the present invention is that the procedure is simplified by performing direct mass spectrometry for a full-length protein without randomly degrading the protein using protease such as trypsin, and it is possible to determine the presence of a target protein with remarkably high reliability within a much shorter time than a conventional method of indirectly identifying proteins by collecting mass information on fragments and collecting vast amounts of information on fragmentation trends of various proteins.

In the present specification, the expression "mass of the protein is the same" means that the mass value measured through the mass spectrometry method of the present invention is substantially the same as a reference mass value, for example, a value corresponding to the mass value of beta-lactamase whose amino acid sequence and molecular weight are known and from which 1 to 28 amino acid residues at the N-terminus have been removed. "Substantially the same" means that, for example, the measured Da value or m/z×z value is within the range of the reference mass value±10, more specifically within the range of the reference mass value±7, even more specifically within the range of the reference mass value±5, most specifically within the range of the reference mass value±3.

According to a specific embodiment of the present invention, the method of the present invention further comprises a step of performing ion exchange chromatography on the protein isolated in step (a). As used herein, the term "ion exchange chromatography" refers to a separation and purification method of separating a charged target substance from a heterogeneous mixture using a phenomenon in which ions or charged compounds bind to an ion exchange resin by electrostatic force. Ion exchange chromatography has ion exchange resins to which various functional groups bind, in which the anion exchange resin has a positively charged functional group and thus combines with a negatively charged target substance in the mixture by electrostatic attraction, and the cation exchange resin binds specifically to a positively charged target substance.

According to a specific embodiment of the present invention, the ion exchange chromatography used in the present invention is anion exchange chromatography. The anion exchange resin used in the present invention may have, for example, a diethylaminoethyl (DEAE) or quaternary ammonium functional group, but is not limited thereto, and any conventional cationic functional group that provides a positive charge to the support may be used without limitation. Strongly basic anion exchange groups include, for example, Q Sepharose Fast Flow, Q Sepharose High Performance, Resource Q, Source 15Q, Source 30Q, Mono Q, Mini Q, Capto Q, Capto Q ImpRes, Q HyperCel, Q Cermic HyperD F, Nuvia Q, UNOsphere Q, Macro-Prep High Q, Macro-Prep 25 Q, Fractogel EMD TMAE(S), Fractogel EMD TMAE Hicap (M), Fractogel EMD TMAE (M), Eshmono Q, Toyopearl QAE-550C, Toyopearl SuperQ-650C, Toyopearl GigaCap Q-650M, Toyopearl Q-600C AR, Toyopearl SuperQ-650M, Toyopearl SuperQ-650S, TSKgel SuperQ-5PW (30), TSKgel SuperQ-5PW (20), and TSKgel SuperQ-5PW, but are not limited thereto, and any anion exchange resins known in the art may be used.

According to a specific embodiment of the present invention, beta-lactamase that is detected by the method of the present invention is a CTX-M protein.

More specifically, the CTX-M protein is at least one protein selected from the group consisting of CTX-M1 to CTX-M7, CTX-M9, CTX-M10, CTX-M12 to CTX-M17, CTX-M19 to CTX-M24, CTX-M27 to CTX-M38, CTX-M40 to CTX-M44, CTX-M46 to CTX-M56, CTX-M58 to CTX-M69, CTX-M71 to CTX-M77, CTX-M79 to CTX-M88, CTX-M90, CTX-M92, CTX-M93, CTX-M95 to CTX-M105, CTX-M110 to CTX-M117, CTX-M121 to CTX-M127, CTX-M129 to CTX-M132, CTX-M134, CTX-M136 to CTX-M139, CTX-M141, CTX-M142, CTX-M144, CTX-M146 to CTX-M148, CTX-M150, CTX-M155 to CTX-M159, CTX-M161 to CTX-M184, CTX-M186 to CTX-M204, CTX-M206 to CTX-M210, CTX-M212 to CTX-M216, and CTX-M218 to CTX-M226, and most specifically, is at least one protein selected from the group consisting of CTX-M1, CTX-M14, CTX-M15, CTX-M27, CTX-M142 and CTX-M186.

More specifically, the CTX-M protein is selected from the group consisting of CTX-M1, CTX-M3, CTX-M10, CTX-M15, CTX-M22, CTX-M23, CTX-M28, CTX-M32 to CTX-M34, CTX-M36, CTX-M42, CTX-M52 to CTX-M55, CTX-M58, CTX-M61, CTX-M62, CTX-M64, CTX-M69, CTX-M71, CTX-M72, CTX-M79, CTX-M80, CTX-M82, CTX-M88, CTX-M101, CTX-M103, CTX-M114, CTX-M116, CTX-M117, CTX-M123, CTX-M127, CTX-M132, CTX-M136, CTX-M138, CTX-M142, CTX-M144, CTX-M146, CTX-M150, CTX-M155 to CTX-M158, CTX-M166, CTX-M167, CTX-M169, CTX-M170, CTX-M172, CTX-M173, CTX-M175 to CTX-M184, CTX-M187 to CTX-M190, CTX-M193, CTX-M197, CTX-M199, CTX-M201 to CTX-M204, CTX-M206 to CTX-M209, CTX-M212, CTX-M216, CTX-M218, CTX-M220, CTX-M222, and CTX-M225.

Most specifically, the CTX-M protein is selected from the group consisting of CTX-M1, M14, M15, M27, M142 and M186.

According to a specific embodiment of the present invention, step (a) of the present invention is performed by adding a surfactant to the biological sample.

As described above, in the present invention, direct mass spectrometry of a full-length protein is possible by top-down mass spectrometry without a fragmentation process using a protease. The present inventors have found that, when a surfactant is added to the biological sample to be analyzed, the intact full-length protein present in the cell membrane or cytoplasm may be encapsulated, so that the target protein may be quickly and accurately identified without randomly degrading the protein by an enzyme.

In the present invention, ionic, nonionic and zwitterionic surfactants may all be used without limitation as long as they are general surfactants capable of forming micelles sufficient to encapsulate full-length proteins, Examples of ionic surfactants that may be used in the present invention include, but are not limited to, sodium deoxycholate (DOC), Medialan A, Quaternium-60, cetylpyridinium chloride, cetylpyridinium bromide, cetyltrimetylammonium chloride, cetyltrimetylammonium bromide, and Gardinol.

Examples of nonionic surfactants that may be used in the present invention include, but are not limited to, n-octyl-β-D-glucopyranoside (OG), n-octyl-β-D-thioglucopyranoside (OTG), octyl glucose neopentyl glycol (OGNG), n-dodecyl-β-D-maltopyranoside (DDM), and n-dodecyl-β-D-thiomaltopyranoside (DDTM).

Examples of zwitterionic surfactants that may be used in the present invention include, but are not limited to, cocamidopropyl betaine, lauramidopropyl betaine, lauryl betaine, coco-betaine, myristyl betaine, cocodimethylcarboxymethyl betaine, lauryl dimethyl carboxymethyl betaine, cocamidopropyl hydroxysultaine, coco-hydroxysultaine, coco-sultaine, erucamidopropyl hydroxysultaine, hydroxysultaine, lauramidopropyl hydroxysultaine, lauryl hydroxysulfaine, lauryl sultaine, methoxycinnamidopropyl hydroxysultaine, myristamidopropyl hydroxysultaine, oleamidopropyl hydroxysultaine, and tallowamidopropyl hydroxysultaine.

The surfactant of the present invention may be used together with a lysis buffer in the step of lysing the cells to isolate the protein expressed by the pathogenic strain.

According to a specific embodiment of the present invention, step (a) of the present invention is performed by applying osmotic pressure to the biological sample. According to the present invention, for efficient direct mass spectrometry of the target protein by top-down mass spectrometry, alternatively or additionally to the above-described method of treating the biological sample with the surfactant, the target protein may be isolated by applying osmotic stimulation to the cells contained in the biological sample to induce osmotic lysis of the cells.

As used herein, the term "osmotic lysis" refers to a process of lysing cells by allowing excess water to diffuse into the cells through osmotic imbalance caused by adding a hypotonic solution to the cells. As the hypotonic solution, a low-concentration solution having a concentration difference from a cell or a cell culture medium enough to allow a sufficient amount of water for cell lysis to flow thereinto may be used without limitation, and for example, distilled water may be used.

According to a specific embodiment of the present invention, step (b) of the present invention is performed using a mass spectrometry method selected from the group consisting of matrix-assisted laser desorption/ionization time of flight (MALDI-TOF) mass spectrometry, surface enhanced laser desorption/ionization time of flight (SELDI-TOF) mass spectrometry, electrospray ionization time-of-flight (ESI-TOF) mass spectrometry, liquid chromatography-mass spectrometry (LC-MS), and liquid chromatography-mass spectrometry/mass spectrometry (LC-MS/MS).

More specifically, it is performed using MALDI-TOF mass spectrometry.

MALDI-TOF mass spectrometry is a method in which a sample supported by a matrix is desorbed and ionized by irradiation with a laser, and then the molecular weights of the generated ions are analyzed by measuring the time (Time-of-Flight) taken for the ions to reach a detector. According to this method, it is possible to quickly and accurately measure the mass of a large biomolecule such as a protein, because fragmentation of the target material does not occur. When the ionized molecule is accelerated by an electric field and the flight time is measured, a mass-to-charge ratio (m/z) is generated, and the molecular weight of the target material may be determined through this m/z value. For example, when $m/z=30{,}000$ ($z=+1$) or 15,000 ($z=+2$), the molecular weight becomes $m/z \times z=30{,}000$.

According to a specific embodiment of the present invention, it is determined that, when one or more mass values (m/z×z) selected from the group consisting of 28210, 28287, 28166, 28164, 28203, 28116, 27946, 28153, 28089, 27974, 28108, 27888, 27973, 27964, 28321, 27932, 28165, 28197, 28044, 27916, 28107, 28167, 28273, 28152, 28081, 28212, 28277, 28182, 28139, 28043, 27819, 27810, 28170, 28298, 28356, 28027, 28073, 28001, 28099, 28000, 27974, 28184, 28148, 28136, 28314, 28214, 28263, 28181, 28211, 28156, 28046, 28071, 27947, 28180, 28121, 28154, 28067, 28006, 28291, 28261, 28307, 28135, 28194, 27998, 28134, 27983, 27944, 27958, 28008, 28018, 28002, 28317, 27931, 28289, 28095, 28033, 27798, 28005, 28193, 28059, 28024, 27948, 28109, 28229, 28042, 27852, 28345, 28238, 27992, 28053, 28036, 28094, 28050, 27915, 28260, 28014, 28218, 28092, 28138, 28240, 28078, 28151, 28140, 28131, 28150, 27975, 27889, 27985, 28125, 28313, 28023, 28120, 28178, 28198, 28090, 27976, 28025, 28122, 28224, 27917, and values within the ranges of these values±5 are detected as a result of the mass spectrometry, a pathogenic strain having resistance to beta-lactam antibiotics is present in the biological sample.

According to the present invention, the mass values are the mass values of the above-described 205 CTX-M proteins from which 28 amino acid residues at the N-terminus have been removed. Thus, it may be determined that, when any one or more of these mass values are detected as a result of the mass spectrometry, the subject has been infected with a strain expressing one or more of the above-described 205 CTX-M proteins, that is, a pathogenic strain having resistance to beta-lactam antibiotics.

According to a specific embodiment of the present invention, the mass values (m/z×z) additionally include a mass value that is increased by 16 or 32 from each mass value.

As shown in the Examples below, the present inventors have found that one or two methionine residues in the CTX-M protein may exist in an oxidized state. Thus, according to the present invention, even when molecular weights that increased by one oxygen atom (16) or two oxygen atoms (32) from the above-listed mass values are measured, it may be determined that a strain expressing the CTX-M protein is present in the sample, whereby it is possible to more closely detect the beta-lactam antibiotic resistance of the strain.

According to another aspect of the present invention, the present invention provides a method for identifying a protein involved in resistance to β-lactam antibiotics in a biological sample, the method comprising the steps of:

(a) isolating a protein expressed by a pathogenic strain in a biological sample isolated from a subject;

(b) performing mass spectrometry on the isolated protein by a top-down method; and (c) determining the type of protein involved in resistance to beta-lactam antibiotics, which is contained in the biological sample, by comparing the result of the mass spectrometry with a mass value selected from the group consisting of the mass values (m/z×z) of β-lactamases listed in Table 1 below, from which 28 amino acid residues at the N-terminus have been removed, values within the ranges of the mass values±5, values that increased by 16 from the mass values, and values that increased by 32 from the mass values.

TABLE 1

| Protein | Mass value |
|---|---|
| CTX-M1 | 28210 |
| CTX-M2 | 28287 |
| CTX-M3 | 28166 |
| CTX-M4 | 28164 |

TABLE 1-continued

| Protein | Mass value |
|---|---|
| CTX-M5 | 28203 |
| CTX-M6 | 28116 |
| CTX-M7 | 28166 |
| CTX-M9 | 27946 |
| CTX-M10 | 28166 |
| CTX-M12 | 28153 |
| CTX-M13 | 28089 |
| CTX-M14 | 27974 |
| CTX-M15 | 28108 |
| CTX-M16 | 27888 |
| CTX-M17 | 27973 |
| CTX-M19 | 27964 |
| CTX-M20 | 28321 |
| CTX-M21 | 27932 |
| CTX-M22 | 28165 |
| CTX-M23 | 28197 |
| CTX-M24 | 28044 |
| CTX-M27 | 27916 |
| CTX-M28 | 28107 |
| CTX-M29 | 28108 |
| CTX-M30 | 28167 |
| CTX-M31 | 28273 |
| CTX-M32 | 28152 |
| CTX-M33 | 28081 |
| CTX-M34 | 28212 |
| CTX-M35 | 28277 |
| CTX-M36 | 28182 |
| CTX-M37 | 28139 |
| CTX-M38 | 28043 |
| CTX-M40 | 27819 |
| CTX-M41 | 27810 |
| CTX-M42 | 28170 |
| CTX-M43 | 28298 |
| CTX-M44 | 28356 |
| CTX-M46 | 28027 |
| CTX-M47 | 28073 |
| CTX-M48 | 28001 |
| CTX-M49 | 28099 |
| CTX-M50 | 28000 |
| CTX-M51 | 27974 |
| CTX-M52 | 28184 |
| CTX-M53 | 28148 |
| CTX-M54 | 28197 |
| CTX-M55 | 28136 |
| CTX-M56 | 28314 |
| CTX-M58 | 28214 |
| CTX-M59 | 28263 |
| CTX-M60 | 28181 |
| CTX-M61 | 28211 |
| CTX-M62 | 28156 |
| CTX-M63 | 28046 |
| CTX-M64 | 28081 |
| CTX-M65 | 28071 |
| CTX-M66 | 28166 |
| CTX-M67 | 27947 |
| CTX-M68 | 28180 |
| CTX-M69 | 28121 |
| CTX-M71 | 28154 |
| CTX-M72 | 28067 |
| CTX-M73 | 28006 |
| CTX-M74 | 28291 |
| CTX-M75 | 28287 |
| CTX-M76 | 28261 |
| CTX-M77 | 28307 |
| CTX-M79 | 28135 |
| CTX-M80 | 28194 |
| CTX-M81 | 27998 |
| CTX-M82 | 28134 |
| CTX-M83 | 27983 |
| CTX-M84 | 27944 |
| CTX-M85 | 27958 |
| CTX-M86 | 28008 |
| CTX-M87 | 28018 |
| CTX-M88 | 28089 |
| CTX-M90 | 28002 |
| CTX-M92 | 28317 |
| CTX-M93 | 27931 |
| CTX-M95 | 28289 |

TABLE 1-continued

| Protein | Mass value |
|---|---|
| CTX-M96 | 28095 |
| CTX-M97 | 28287 |
| CTX-M98 | 27944 |
| CTX-M99 | 28033 |
| CTX-M100 | 27798 |
| CTX-M101 | 28134 |
| CTX-M102 | 27974 |
| CTX-M103 | 28135 |
| CTX-M104 | 28001 |
| CTX-M105 | 28002 |
| CTX-M110 | 28089 |
| CTX-M111 | 28005 |
| CTX-M112 | 27944 |
| CTX-M113 | 28002 |
| CTX-M114 | 28108 |
| CTX-M115 | 28317 |
| CTX-M116 | 28193 |
| CTX-M117 | 28139 |
| CTX-M121 | 27946 |
| CTX-M122 | 28059 |
| CTX-M123 | 28121 |
| CTX-M124 | 28287 |
| CTX-M125 | 28024 |
| CTX-M126 | 27948 |
| CTX-M127 | 28109 |
| CTX-M129 | 27944 |
| CTX-M130 | 28024 |
| CTX-M131 | 28229 |
| CTX-M132 | 28042 |
| CTX-M134 | 27946 |
| CTX-M136 | 28194 |
| CTX-M137 | 27852 |
| CTX-M138 | 28184 |
| CTX-M139 | 28108 |
| CTX-M141 | 28345 |
| CTX-M142 | 28107 |
| CTX-M144 | 28152 |
| CTX-M146 | 28238 |
| CTX-M147 | 27992 |
| CTX-M148 | 28053 |
| CTX-M150 | 28167 |
| CTX-M155 | 28036 |
| CTX-M156 | 28094 |
| CTX-M157 | 28050 |
| CTX-M158 | 28238 |
| CTX-M159 | 27915 |
| CTX-M161 | 28046 |
| CTX-M162 | 28166 |
| CTX-M163 | 28108 |
| CTX-M164 | 28136 |
| CTX-M165 | 28260 |
| CTX-M166 | 28238 |
| CTX-M167 | 28212 |
| CTX-M168 | 28014 |
| CTX-M169 | 28081 |
| CTX-M170 | 28107 |
| CTX-M171 | 28218 |
| CTX-M172 | 28092 |
| CTX-M173 | 28138 |
| CTX-M174 | 27916 |
| CTX-M175 | 28240 |
| CTX-M176 | 28078 |
| CTX-M177 | 28151 |
| CTX-M178 | 28138 |
| CTX-M179 | 28140 |
| CTX-M180 | 28138 |
| CTX-M181 | 28131 |
| CTX-M182 | 28136 |
| CTX-M183 | 28135 |
| CTX-M184 | 28095 |
| CTX-M186 | 28108 |
| CTX-M187 | 28170 |
| CTX-M188 | 28138 |
| CTX-M189 | 28078 |
| CTX-M190 | 28150 |
| CTX-M191 | 27975 |
| CTX-M192 | 27944 |
| CTX-M193 | 28138 |

TABLE 1-continued

| Protein | Mass value |
|---|---|
| CTX-M194 | 28108 |
| CTX-M195 | 27889 |
| CTX-M196 | 27985 |
| CTX-M197 | 28094 |
| CTX-M198 | 27974 |
| CTX-M199 | 28125 |
| CTX-M200 | 28313 |
| CTX-M201 | 28023 |
| CTX-M202 | 28120 |
| CTX-M203 | 28194 |
| CTX-M204 | 28178 |
| CTX-M206 | 28139 |
| CTX-M207 | 28166 |
| CTX-M208 | 28166 |
| CTX-M209 | 28120 |
| CTX-M210 | 28138 |
| CTX-M212 | 28198 |
| CTX-M213 | 28090 |
| CTX-M214 | 27976 |
| CTX-M215 | 28025 |
| CTX-M216 | 28138 |
| CTX-M218 | 28122 |
| CTX-M219 | 27976 |
| CTX-M220 | 28139 |
| CTX-M221 | 27900 |
| CTX-M222 | 28224 |
| CTX-M223 | 27917 |
| CTX-M224 | 28108 |
| CTX-M225 | 28138 |
| CTX-M226 | 28136 |

Since the biological sample, protein involved in resistance to antibiotics, and mass measurement method therefor according to the present invention have already been described above, description thereof will be omitted to avoid excessive overlapping.

The present invention provides the mass value of a specific reference from which the N-terminus has been removed, thereby providing not only information on whether the strain has resistance to beta-lactam antibiotics, but also information about the type of protein involved in the resistance, which is expressed by the strain. Through this information, a more specific antibiotic administration strategy for a patient may be established by referring to the beta-lactam antibiotic degradation ability, in vivo activity and half-life of each resistance protein, whether each protein is degraded by protease, and the like.

Advantageous Effects

The features and advantages of the present invention are summarized as follows:

(a) The present invention provides a method for detecting a pathogenic strain having resistance to beta-lactam antibiotics in a biological sample, and a method for identifying a protein involved in resistance to beta-lactam antibiotics, which is contained in the biological sample.

(b) According to the present invention, it is possible to directly identify an N-terminal truncated extended spectrum β-lactamase (ESBL) protein by mass spectrometry, thereby making it possible to quickly and accurately determine not only whether a pathogenic strain has resistance to antibiotics, but also the type of protein involved in the resistance. Thus, the present invention may be advantageously used to quickly establish an appropriate strategy for antibiotic administration at an early stage of infection.

BRIEF DESCRIPTION OF DRAWINGS

FIGS. 5A and 5B indicate CTX-M protein peptides identified as MS-GF+, and shows a table (FIG. 5A) showing information on the position and sequence of each identified peptide and alignment results (FIG. 5B) that comparatively show the identification ranges (grey) of representative CTX-M proteins identified in the strain and the oxidized methionine residues (bold and underlined).

MODE FOR INVENTION

Hereinafter, the present invention will be described in more detail with reference to examples. These examples serve merely to illustrate the present invention in more detail, and it will be apparent to those skilled in the art that the scope of the present invention according to the subject matter of the present invention is not limited by these examples.

EXAMPLES

Example 1. Cloning of ESBL Gene and Construction of Antibiotic Resistant Strain Based on information about the CTX-M gene sequence (European Molecular Biology Laboratory (EMBL) nucleotide sequence database accession number: CP008736.1, 876 nt) (SEQ ID NO: 1) obtained from the gene for *E. coli* ESBL protein, the following oligonucleotides were prepared.

```
Primer 1:
5'-AACTGCAGGATGGTTAAAAAATCACTGCGTCAG-3' (33 nt)

Primer 2:
5'-GGAATTCTCACAAACCGTTGGTGACGATT-3' (29 nt)
```

Restriction enzyme sites for cloning were added to the oligonucleotides, and an open reading frame (ORF) was created to induce expression directly in a cloning vector.

The target gene was amplified by PCR from the CTX-M template DNA. For PCR, a total of 50 μl of a PCR reaction solution was prepared using 3 μl of template DNA, 1.25 μl of 5' primer, 1.25 μl of 3' primer, 1 μl of dNTPs, and 10 μl of 5× buffer, and then PCR was performed under the following conditions: 1) denaturation—at 98 °C for 10 sec; 2) annealing—at 57 °C for 30 sec; 3) extension—at 72 °C for 30 sec. Cloning for construction of a recombinant plasmid containing the target gene was performed as follows: 1) For the insert gene and the vector, both ends of the DNA were cut into sticky ends using restriction enzymes, and 2) the insert gene was ligated into the vector using DNA ligase. 3) Thereafter, the vector was transformed into *E. coli* (*E. coli* Top10), and 4) recombinant *E. coli* was selected by the white/blue screening method. 5) A recombinant plasmid was extracted from the selected strain, and 6) the extracted plasmid was treated with restriction enzymes, and the DNA size was determined. 7) Finally, the inserted gene was confirmed through DNA sequencing.

Example 2. Analysis of Expression and Size of Target Protein

Figure 1A:
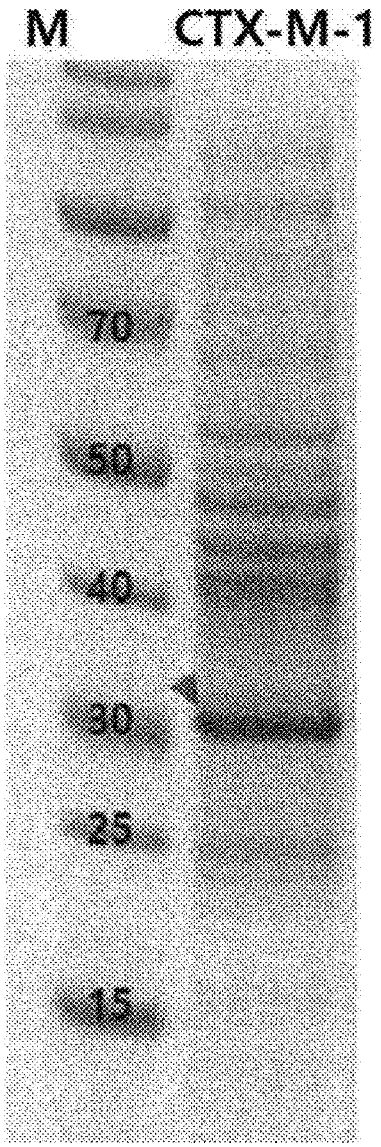
FIGS. 1A and 1B show the results of SDS-PAGE analysis for the expression and sizes of CTX-M proteins derived from an antibiotic-resistant strain, and shows SDS-PAGE results for CTX-M1 protein (FIG. 1A) and CTX-M15 protein (FIG. 1B) as representative examples.
Figure 1B:
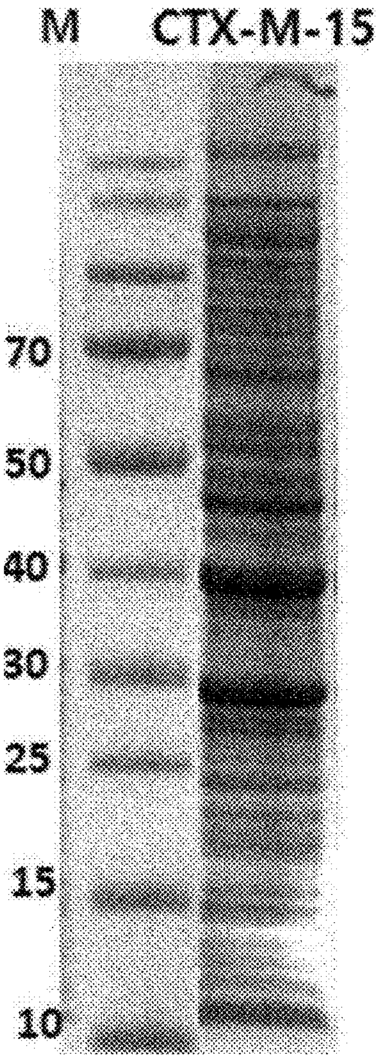

*E. coli* transformed with the plasmid containing the target gene was inoculated into Luria-bertani liquid medium containing 50 mg/L of ampicillin antibiotic, and cultured at 37 °C for 16 hours or more. In order to analyze the expression and size of the target protein, the culture was centrifuged at 4,000 rpm for 15 minutes, and the cells were harvested by removing the supernatant. The harvested cells were added to SDS-sample buffer, heated at 95 °C for 5 min, and centrifuged at 15,000 rpm for 5 min. Using the prepared sample, the expression and size of the target protein were analyzed through SDS-PAGE gel analysis (FIG. 1).

Figure 2A:
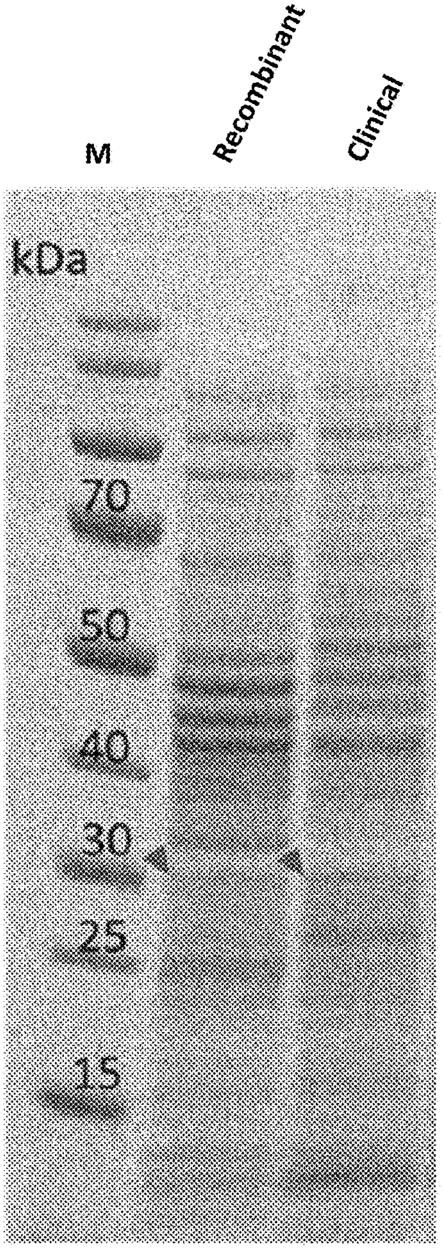
FIGS. 2A and 2B show the results of SDS-PAGE analysis for the expression and size of protein in a recombinant strain containing the CTX-M protein and gene derived from a clinical strain, and indicates the protein difference between a crude extract and a crude enzyme solution, obtained by addition of a nonionic surfactant (FIG. 2A) and an ionic surfactant (FIG. 2B), respectively.

Example 3. Sample Pretreatment Method and Identification of Target Protein from Crude Enzyme Solution (1) Sample Pretreatment with Nonionic Surfactant For sample pretreatment, the culture was centrifuged at 4,000 rpm for 15 minutes, and the cells were harvested by removing the supernatant. To obtain a crude extract, the cells were treated with a buffer solution (0.25 mM Tris-HCl, 2% OG) and incubated at room temperature for 10 minutes. The prepared crude extract was separated into a supernatant (hereinafter referred to as crude enzyme solution) and a precipitate by centrifugation at 15,000 rpm at 4 °C for 10 minutes. From the crude enzyme solution, the expression and size of the target protein were analyzed by SDS-PAGE analysis from (FIG. 2A).

(2) Sample Pretreatment with Ionic Surfactant

Sample pretreatment was performed by the following steps: 1) 100 μl of the expressed cell culture was centrifuged to recover the cells, and 2) the supernatant was removed, and then a buffer solution (0.25 mM Tris-HCl, pH 8.0 and 2% DOC) containing 2% sodium deoxycholate (DOC) as a nonionic surfactant was added to the cells. 3) The suspension was incubated at room temperature for 10 minutes, and 4) centrifuged at 15,000 rpm at 4 °C for 10 minutes to obtain a crude enzyme solution.

Figure 2B:
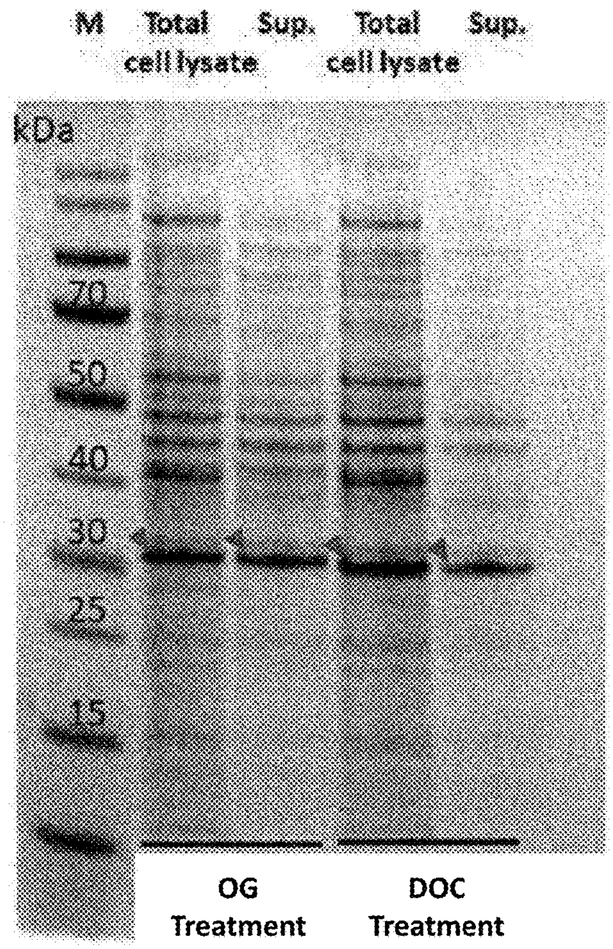

From the crude extract and the crude enzyme solution, obtained by treatment with the nonionic surfactant (OG) and the ionic surfactant (DOC), respectively, the expression and size of the protein were analyzed by SDS-PAGE gel analysis (FIG. 2B).

(3) Cell Lysis by Osmotic Pressure

Figure 3:
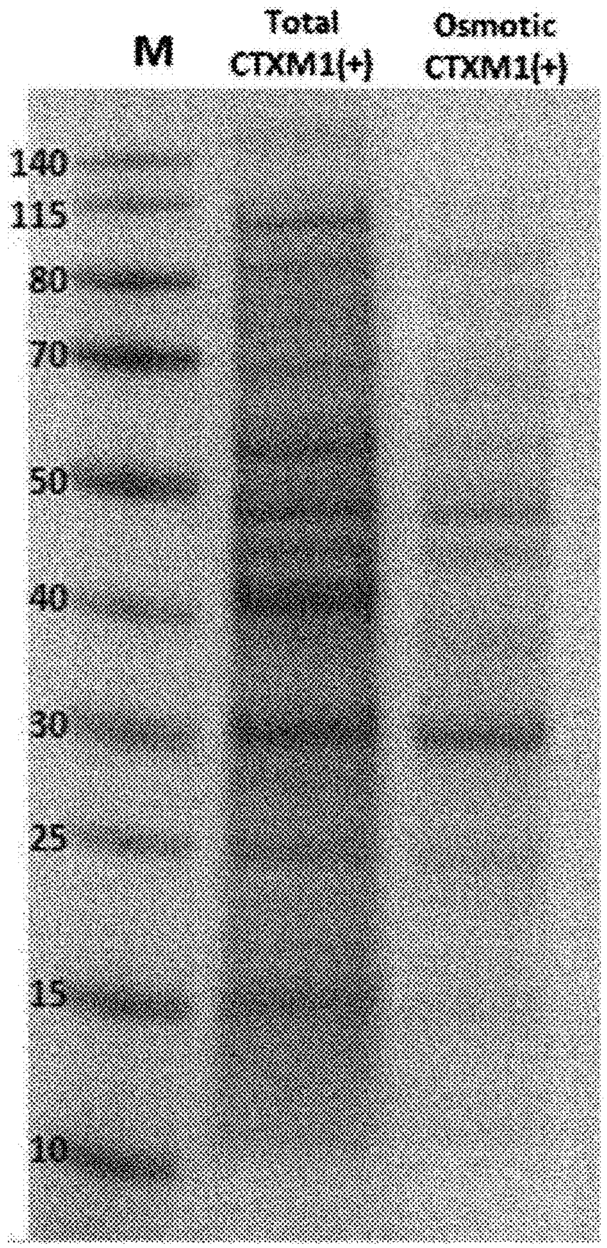
FIG. 3 shows the results of SDS-PAGE analysis for the expression and size of a target protein in a sample pretreated with osmotic stimulation.

The strain culture was added to a washing buffer (pH 8.0 Tris-HCl+500 mM NaCl), and then incubated at room temperature for 10 minutes. Next, the supernatant was removed by centrifugation at 14,000 g for 10 minutes, and triple distilled water was added to the pellet, followed by incubation for 10 minutes. This pretreated sample was further separated into a supernatant (crude enzyme solution) and a precipitate by centrifugation. From the crude enzyme solution, the expression and size of the target protein were analyzed by SDS-PAGE analysis (FIG. 3).

Example 4. Confirmation of Genotype of CTX-M Derived from Clinical Strain and Confirmation of Protein In order to confirm CTX-M derived from a clinical strain, a strain confirmed as positive for ESBL was collected. The collected strain was subjected to colony PCR using the primers used for CTX-M gene amplification. The resulting amplified PCR product was subjected to agar gel electrophoresis to confirm the size of the target gene. The PCR product whose size has been confirmed was subjected to DNA sequencing to confirm the exact genotype of the CTX-M gene.

The strain whose genotype has been confirmed was cultured using LB broth, and SDS-PAGE gel analysis was performed to examine whether CTX-M protein would be expressed. In addition, a recombinant strain containing the CTX-M gene derived from the clinical strain was constructed in the same manner as the existing recombinant strain comprising the vector containing the CTX-M gene, and the recombinant strain was also subjected to SDS-PAGE gel analysis in the same manner as the clinical strain to confirm the size of the actually expressed CTX-M protein (FIG. 3).

Example 5. Separation/Purification of Target Protein

Figure 4:
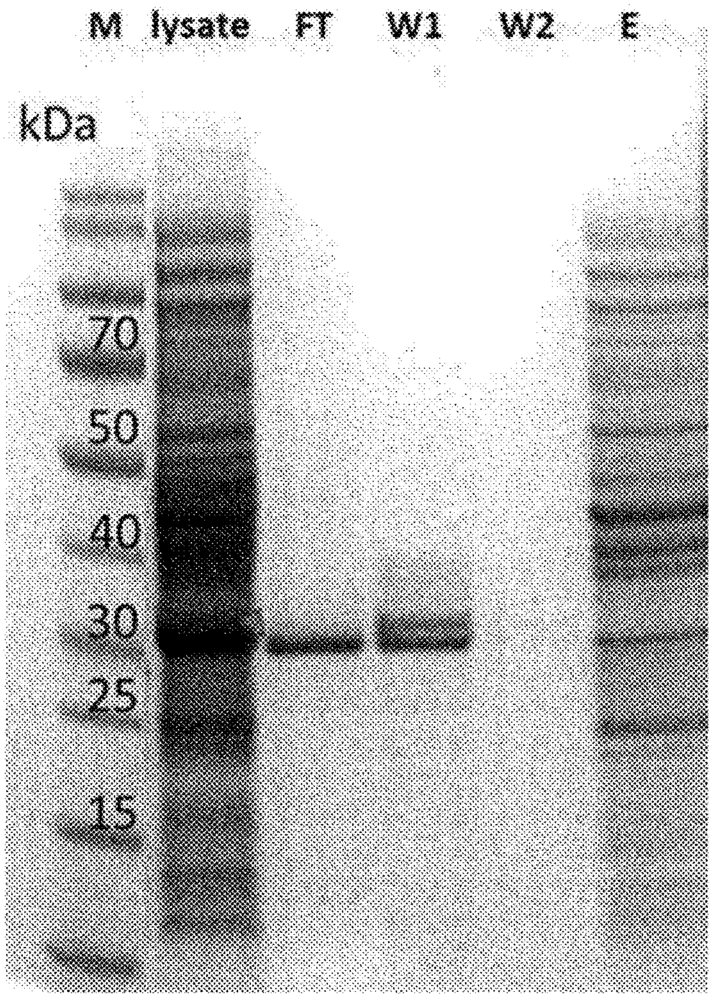
FIG. 4 shows the results of separating and purifying a target protein using ion chromatography.
Figure 6A:
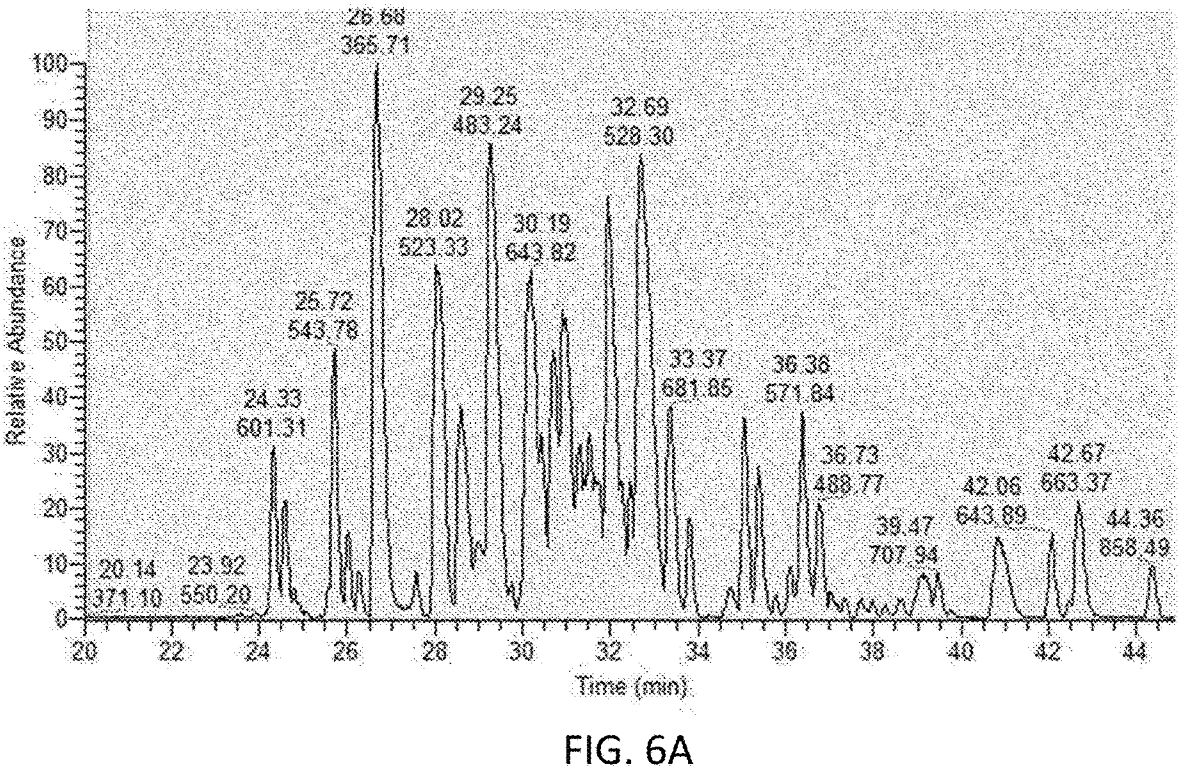
FIGS. 6A, 6B, 6C and 6D show exemplary tandem spectrum results for peptides identified as N-terminal and C-terminal peptides in representative subtype peptides of CTX-M, and shows the separation chromatogram of the CTX-M1 peptide (FIG. 6A), the results of identification of the C-terminal peptide of CTX-M1 (FIG. 6B), the results of identification of the N-terminal peptide of CTX-M1 (FIG. 6C), and the results of identification of the N-terminal peptide of CTX-M15 (FIG. 6D).
Figure 6B:
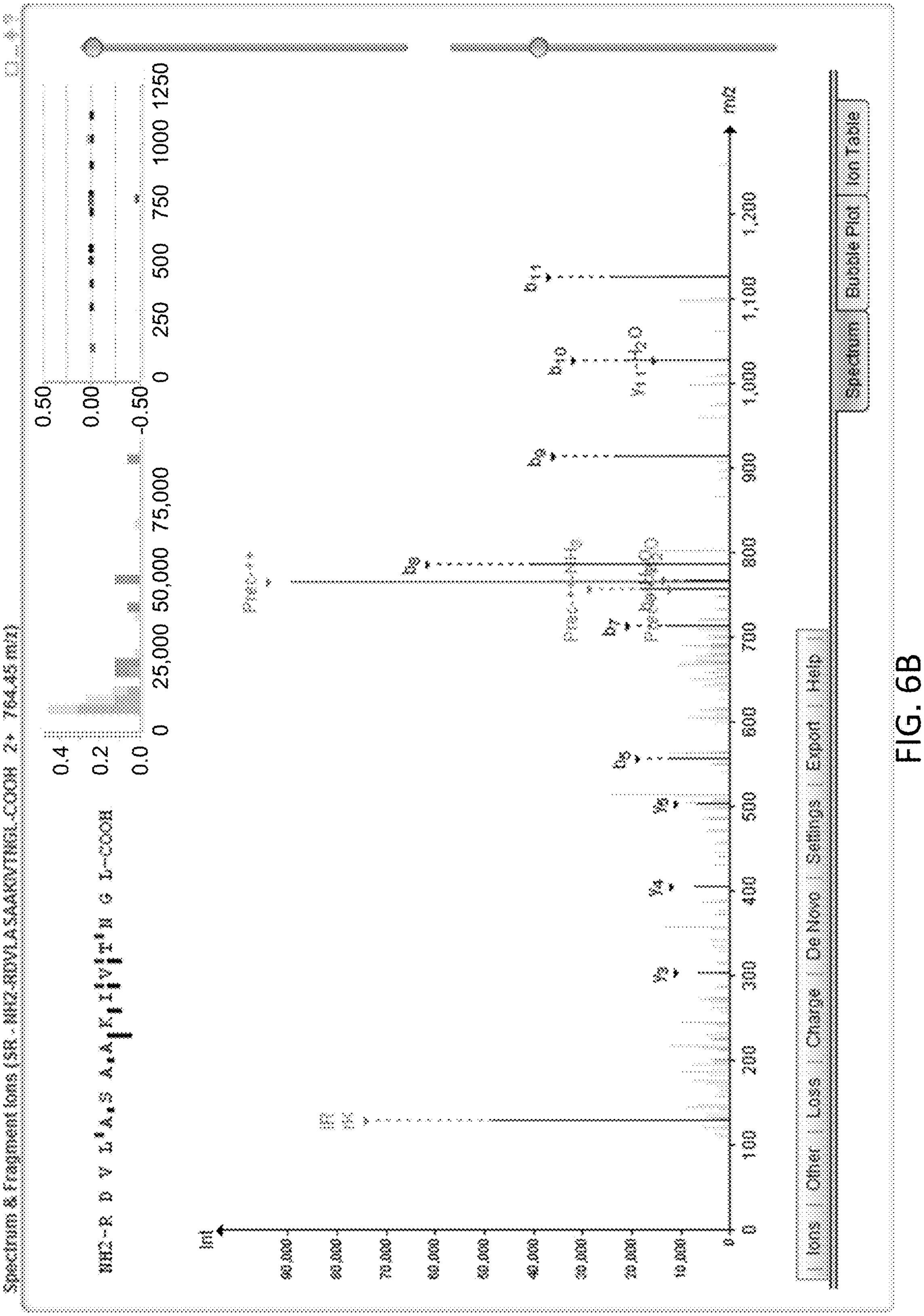
Figure 6C:
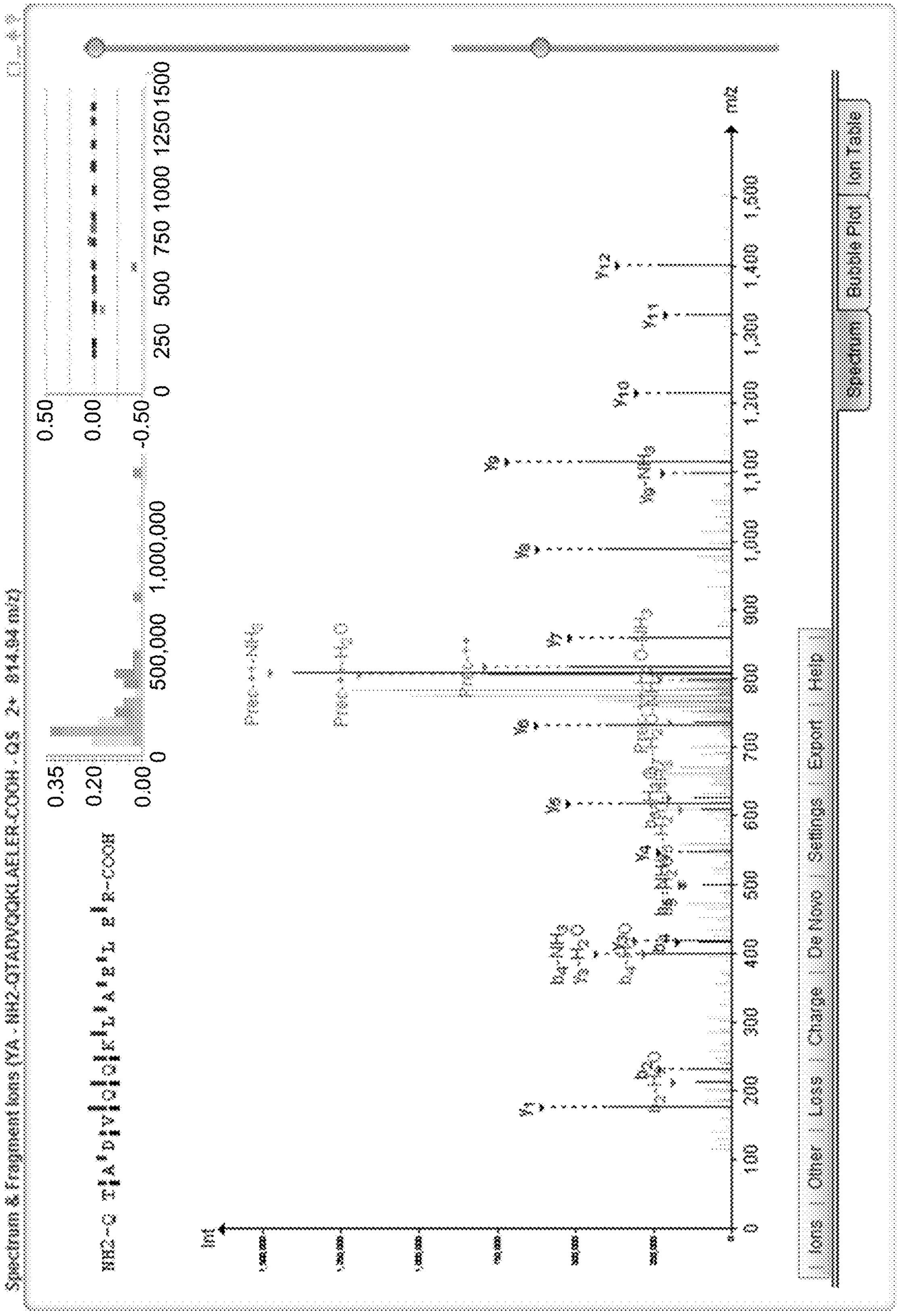
Figure 6D:
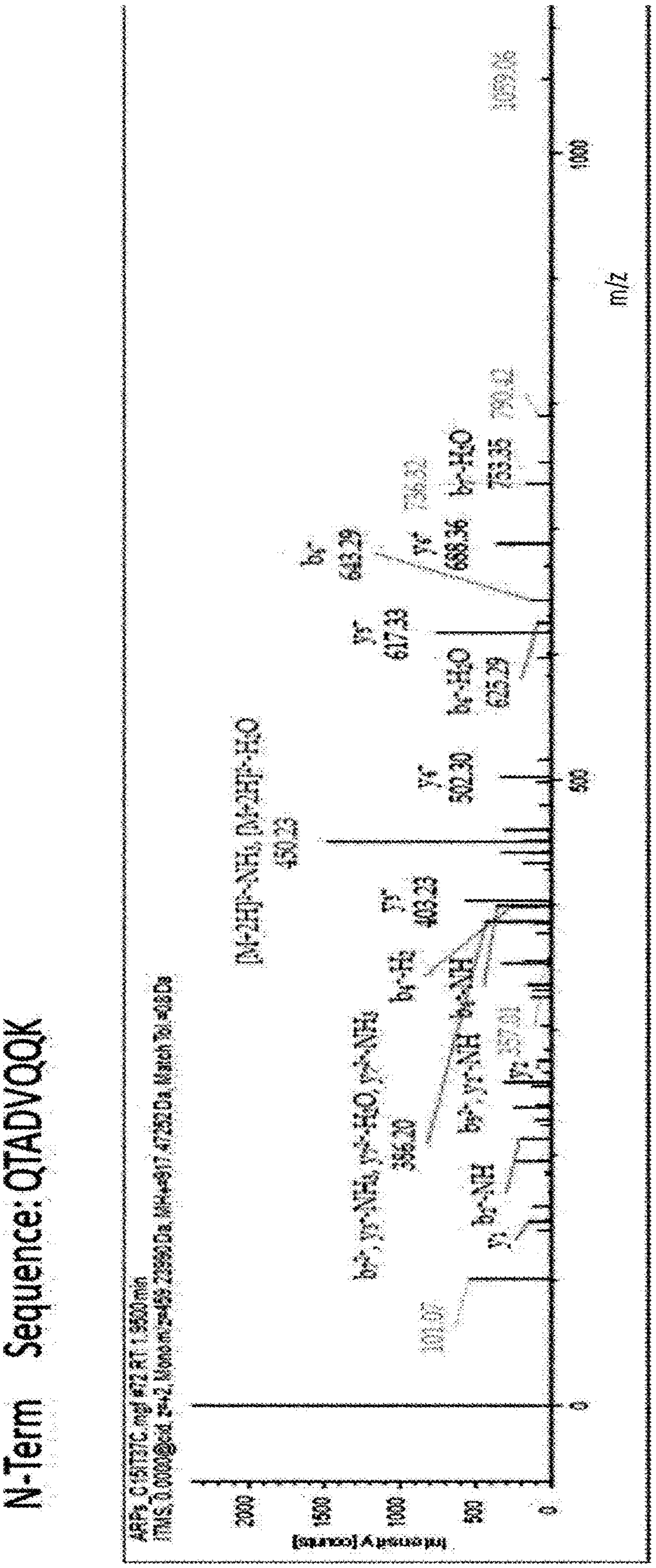

Ion exchange chromatography was used to separate/purify the target protein. Q-resin was used as the ion exchange resin, 500 μl of the crude enzyme solution was loaded into a column containing Q-resin, and then the eluted solution was collected. The column was washed with 1 ml of 20 mM Tris-HCl (pH 8.0) buffer, and eluted with 1M NaCl, 20 mM Tris-HCl (pH 8.0) buffer. The sample collected in each step was subjected to SDS-PAGE gel electrophoresis to confirm the separated/purified zone (FIG. 4). Finally, high-purity CTX-M protein was separated/purified from the cell lysate using the same method as above.

Example 6. Analysis of Expression and Size of Target Protein

The protein whose expression and size were confirmed on the SDS-PAGE gel was identified using the in-gel digestion method and the nano-LC-MS/MS method, thereby confirming the type of antibiotic resistance protein actually expressed in the strain (FIG. 5A).

(1) In-Gel Digestion

Only the band portion corresponding to the size of the target protein on the SDS-PAGE gel was obtained, and the stained gel was destained. The destained gel was subjected to a reduction/alkylation process, and then the protein was selectively digested using a trypsin enzyme. The digested peptides were recovered and desalted using DK-Tip (C18 Tip).

(2) Nano-LC-MS/MS

In order to confirm the sequence and range of the active protein expressed in the strain, nano liquid chromatography and high-resolution mass spectrometry were performed (Q-Exactive HF-X mass spectrometry system). The desalted peptide sample was dissolved with 0.1% formic acid solution and then loaded into a column. The peptide sample was separated using a C18 column (75 μm×70 cm) and nanoflow liquid chromatography. The gradient conditions for sample loading and separation used at this time are as follows:

buffer A: 0.1% formic acid in water/buffer B: 0.1% formic acid in acetonitrile sample loading: from 0 to 5 min, 5% (B), 5 μL/min flow rate concentration gradient for separation:

from 5 to 7 min, from 5% to 10% (B), 300 nL/min flow rate from 7 to 38 min, from 10% to 40% (B), 300 nL/min flow rate from 38 to 38.5 min, from 40% to 80% (B), 300 nL/min flow rate from 38.5 to 39.5 min, 80% (B), 300 nL/min flow rate from 39.5 to 40 min, from 80% to 5% (B), 300 nL/min flow rate from 40 to 60 min, 5% (B), 300 nL/min flow rate The parameters of the mass spectrometer used at this time are as follows:

resolution: Full MS 60,000, MS2 30,000

Full MS: 350 to 2,000 m/z, 100 msec

MS2: 50 msec, NCE 28, 1, ionized materials with a charge state of >6 were excluded from MS2 analysis As software for identifying peptides and proteins based on bottom-up data, the 'MS-GF+' search engine developed at San Diego State University, USA was used, and protein/peptide identification was based on a FDR (false discovery rate) of 1%. Among proteins from *E. coli*, CTX-M protein was identified, and 143 peptides were identified (total coverage of 90.38%). In addition, peptides in which one or two methionine among six methionine residues (71, 78, 120, 138, 189, and 214) are in oxidized form were also identified. Specifically, the N-terminal sequence peptide consisting of residues 1 to 28 was not detected, and when the sequence except for residues 1 to 28 was considered, peptides spanning all sequence ranges were identified, suggesting that the coverage was 100% (gray background in FIG. 5B).

Figure 7:
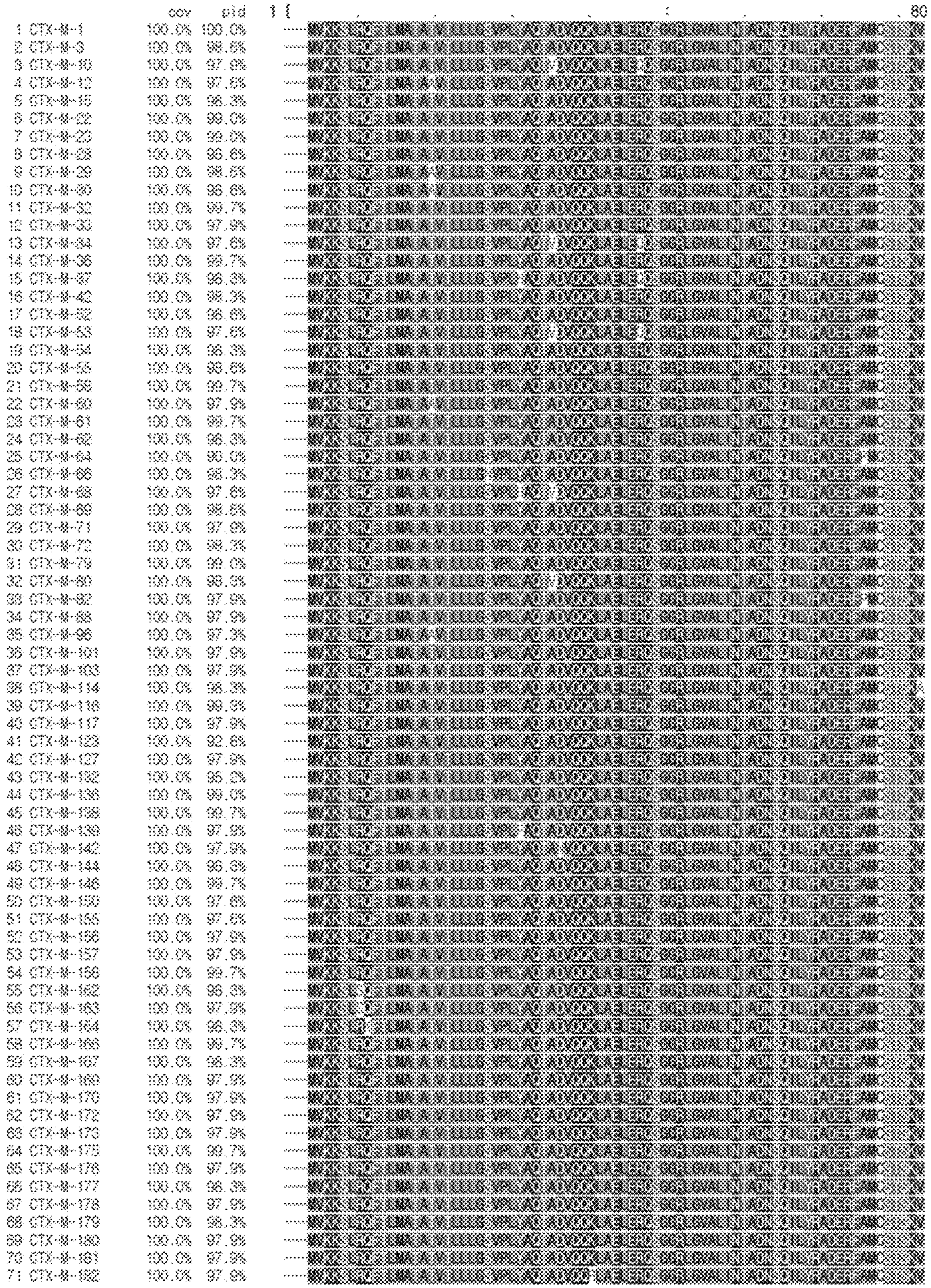
FIG. 7 shows examples of the results of multiple alignment analysis of the CTX-M protein amino acid sequences, performed using the Clustal Omega program, and the results of identification of the conservative amino acid sequences.

(3) Identification of N-Terminal and C-Terminal Sequences (FIG. 7)

```
-N-terminal sequence:
(A)/QTADVQQK (semi-tryptic)

-C-terminal sequence:
(R)/RDVLASAAKIVTNGL-(semi-tryptic)
```

Example 7. Amino Acid Sequencing and Characterization of CTX-M Protein

Based on the MS2 results of Example 3, multiple alignment analysis was performed on all 205 CTX-M proteins known to date in the National Center for Biotechnology Information (NCBI) database (FIG. 7). As a result, 98 CTX-M proteins in which 97.6% or more of the full-length amino acid sequence is conserved were identified, and 82 CTX-M proteins containing the same N-terminal peptide (1 to 28 a.a.) as CTX-M-1 were identified. All 82 proteins identified were characterized by a sequence consisting of 291 amino acids.

Example 8. Target Protein Identification Using Mass Spectrometry (Top-Down Method)

To determine the mass value of the active protein expressed in the strain, top-down mass spectrometry was performed. To confirm the exact mass value of the protein, the crude protein extract derived from the strain was used, and a top-down LC-MS/MS system (Nano-LC and Q-Exactive HF-X mass spectrometry system) was used.

(1) Separation of Crude Protein Extract

About 0.1 μg of a protein sample was mixed with a 1% formic acid solution at a ratio of 1:1 and adjusted to approximately pH 3, and then the sample was loaded into a column. The crude protein extract was separated using a column (150 μm×20 cm) packed with PLRP-S resin and nanoflow liquid chromatography. The gradient conditions for sample loading and separation used at this time are as follows.

Figure 8A:
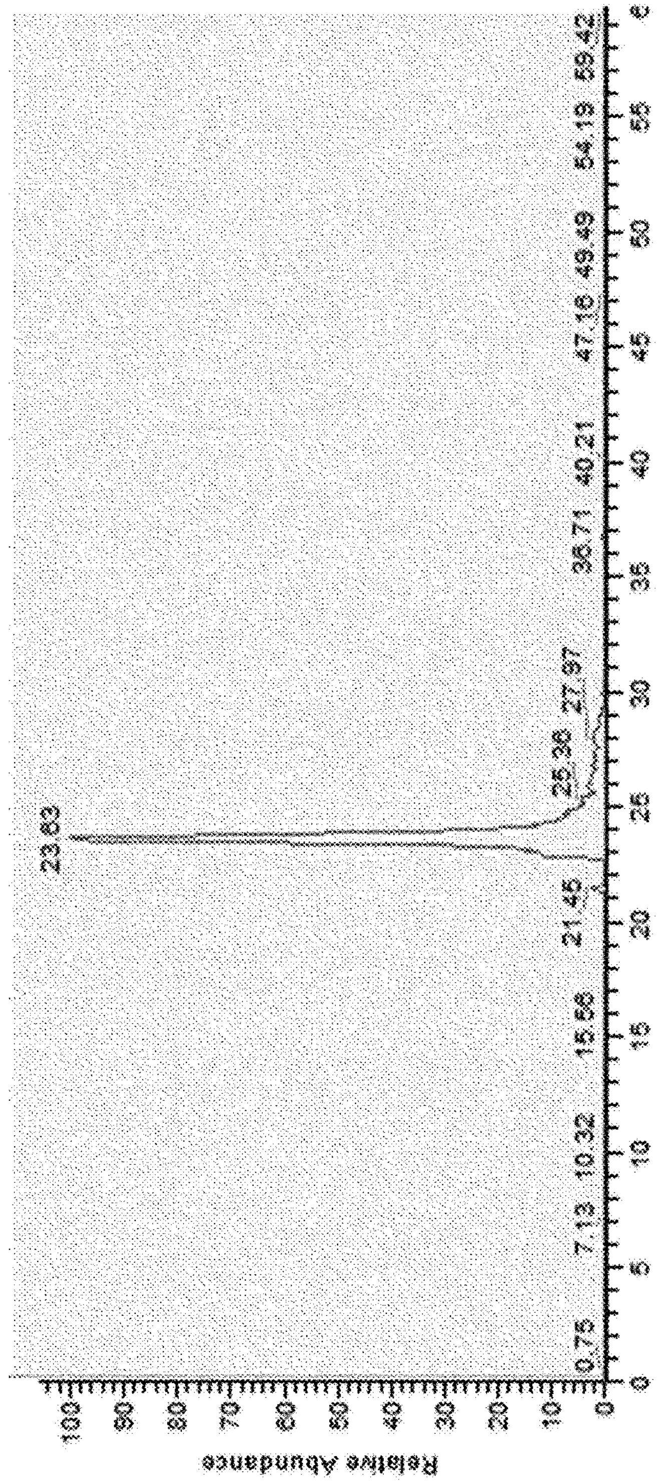
FIGS. 8A, 8B and 8C show the results of protein identification performed using a high-resolution mass spectrometer, and shows the elution chromatogram of the CTX-M protein (eluted at RT 23.63 min) (FIG. 8A), and the mass spectrum of the multi-charged CTX-M protein (monoisotopic mass−28,192 m/z×z, average molecular weight−28,210 m/z×z) (FIG. 8B), and the tandem spectra of CTX-M protein ions with a charge state of 25 and an example of identification results of the 29-291 a.a. sequence (top/average molecular weight−28,210 m/z×z: E=1.3E-27, bottom/average molecular weight 28,210+32 m/z×z: E=2.36E-25) (FIG. 8C).
Figure 8B:
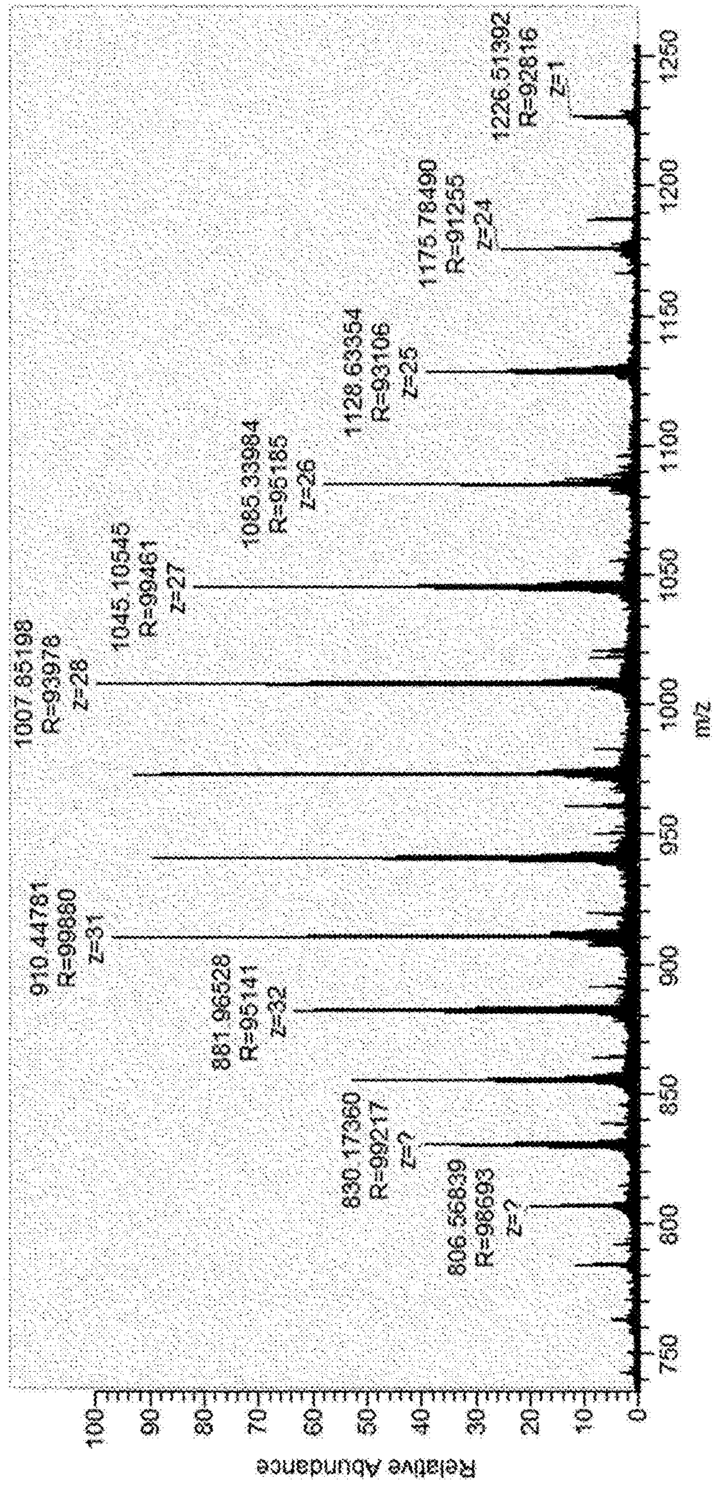
Figure 8C:
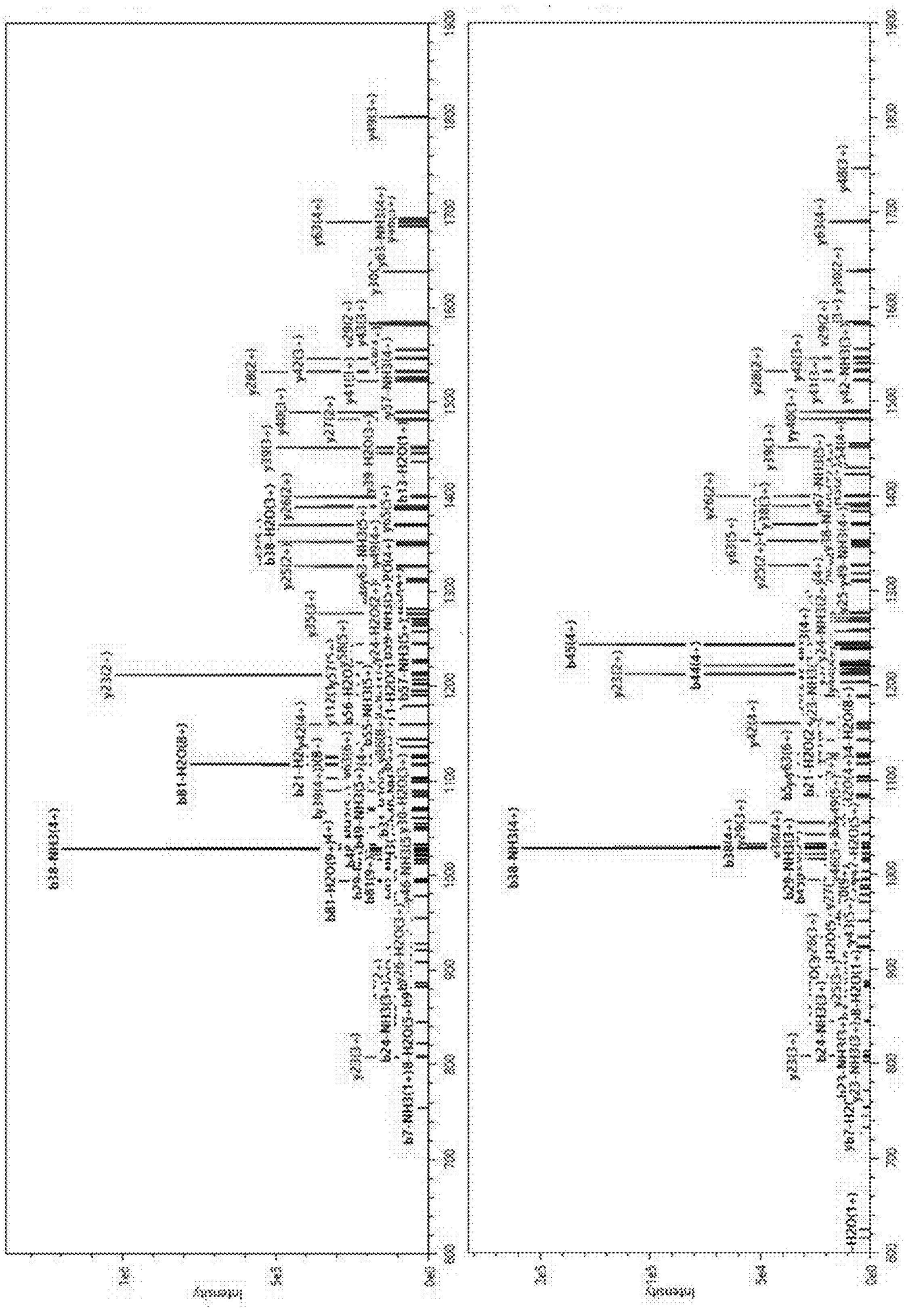

Buffer A: 0.1% formic acid in water/buffer B: 0.1% formic acid in acetonitrile sample loading: from 0 to 10 min, 5% (B), 5 μL/min flow rate Concentration gradient for separation:

from 10 to 10.01 min, from 5% to 10% (B), 300 nL/min flow rate from 10.01 to 40 min, from 10% to 40% (B), 300 nL/min flow rate from 40 to 41 min, from 40% to 80% (B), 300 nL/min flow rate from 41 to 42 min, 80% (B), 300 nL/min flow rate from 42 to 43 min, from 80% to 5% (B), 300 nL/min flow rate from 43 to 60 min, 5% (B), 300 nL/min flow rate (2) Mass Spectrometry of CTX-M Protein Using High-Resolution Mass Spectrometry Using the protein mode analysis method with the Q-Exactive HF-X mass spectrometer, the mass values of the intact proteins and the tandem mass spectra of the proteins were obtained and identified (FIGS. 8A, 8B and 8C). The parameters used in this case are as follows.

Resolution: use of Full MS 240,000, MS2 120,000

Full MS: 620 to 2,400 m/z, 100 msec

MS2: use of 1 microscan, 1,000 msec, NCE 50; ionized materials with a charge state of 1 to 8 were excluded from MS2 analysis.

Software for identifying proteins based on top-down data, 'Informed Proteomics' developed by US PNNL (Pacific Northwest National Laboratory) was used. Several multi-charged CTX-M protein peaks appeared at around 23.63 minutes (FIG. 5 FIG. 8A), and it was confirmed that a representative mass value obtained by deconvolution of the peaks was an average molecular weight of 28,209.69 m/z×z, and 28,192.69 m/z×z as a monoisotopic mass. In addition, other peaks resulting from methionine oxidation were observed (e.g., polypeptides with two oxidized methionines showed an average molecular weight of 28,210+32 m/z×z). They partially coincided with the positions of oxidized methionine residues (71, 78, 120, 138, 189, and 214) within the CTX protein range (29-291 a.a.) obtained through in-gel digestion (bottom-up method). Polypeptides including the N-terminal sequence consisting of residues 1-29 were not observed even in the analysis based on the top-down method.

(3) Mass Spectrometry of CTX-M Protein Using Low-Resolution Mass Spectrometer

Figure 9:
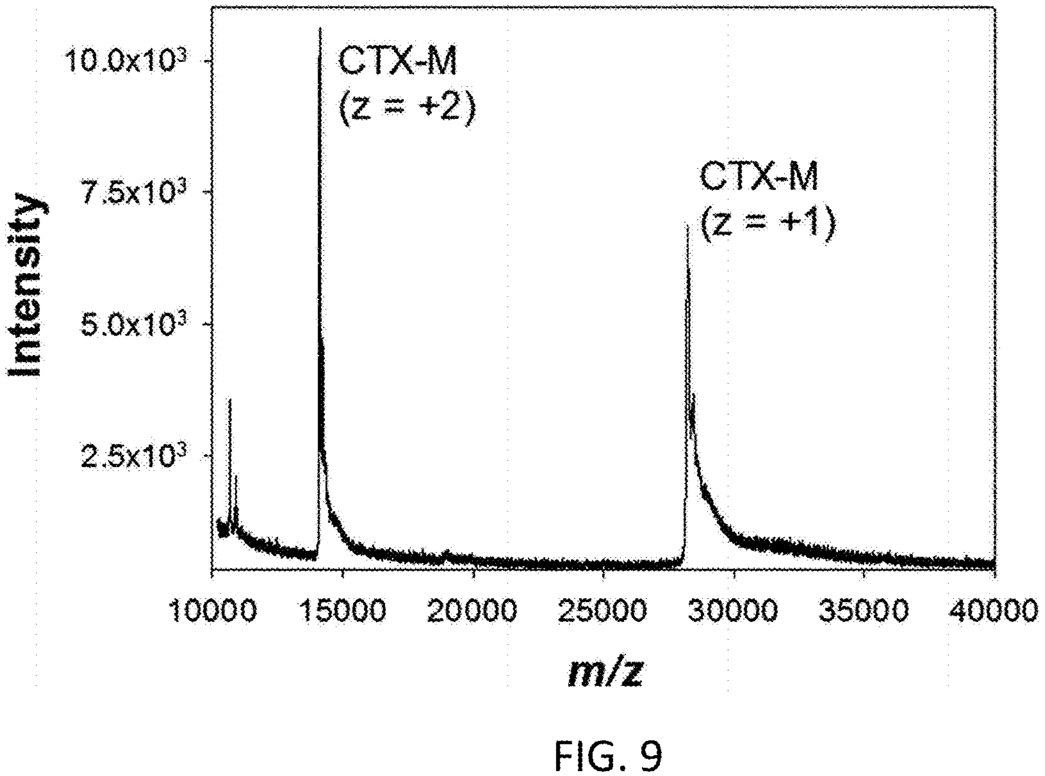
FIG. 9 shows an example of the mass spectrometry spectrum of CTX-M protein, obtained using a low-resolution mass spectrometer (MALDI-TOF).

The mass spectrometry spectrum of CTX-M protein was obtained using the Bruker Biotyper MALDI-TOF MS system. First, 1 μL of a sinapinic acid (SA, present at 10 mg/mL in 0.1% TFA/50% acetonitrile) matrix and about 100 ng of CTX-M protein were placed on the plate spot, dried completely, and subjected to mass spectrometry. At this time, the maximum energy used was 30%, random position acquisition was performed, a total of 2,000 laser shots (40 shots per time) were irradiated, and each spectral data was cumulatively obtained. Mass spectrometry spectra were obtained for the range of 10,000 to 40,000 m/z, and CTX-M protein with a charge state of +1 as well as CTX-M protein with a charge state of +2 were simultaneously detected (FIG. 9).

(4) Comparison of Mass Values of CTX-M Proteins

The exact mass values of the CTX-M proteins were confirmed through the above-described method, and the mass values of the active CTX-M proteins from which the N-terminal peptide has been removed could be confirmed based on the confirmed mass values. Thus, for all CTX-M proteins identified in NCBI, the exact mass value of the active protein can be confirmed through high-resolution or low-resolution mass spectrometry, and it is possible to rapidly and accurately identify various types of CTX-M proteins through mass spectrometry (Table 2).

TABLE 2

Mass data of CTX-M protein

| | Full-length CTX-M protein | | | | Active protein | | | | |
|---|---|---|---|---|---|---|---|---|---|
| CTX-M | Da | Average molecular weight | Monoisotopic mass | PI | Da | Average molecular weight | Monoisotopic mass | PI | N-terminus removed |
| 1 | 31246 | 31245.69 | 31226.29 | 9.25 | 28210 | 28209.95 | 28192.58 | 8.63 | 1-28aa |
| 2 | 31378 | 31377.79 | 31358.23 | 8.91 | 28287 | 28287.02 | 28269.62 | 7.99 | 1-28aa |
| 3 | 31202 | 31201.64 | 3118.26 | 9.25 | 28166 | 28165.90 | 28148.55 | 8.63 | 1-28aa |
| 4 | 31255 | 31254.52 | 31235.00 | 7.86 | 28164 | 28163.75 | 28146.39 | 6.59 | 1-28aa |
| 5 | 31294 | 31293.67 | 31274.17 | 9.12 | 28203 | 28202.90 | 28185.57 | 8.60 | 1-28aa |
| 6 | 31207 | 31206.51 | 31187.07 | 8.61 | 28116 | 28115.74 | 28098.46 | 7.15 | 1-28aa |

TABLE 2-continued

Mass data of CTX-M protein

| CTX-M | Full-length CTX-M protein Da | Full-length CTX-M protein Average molecular weight | Full-length CTX-M protein Monoisotopic mass | Full-length CTX-M protein PI | Active protein Da | Active protein Average molecular weight | Active protein Monoisotopic mass | Active protein PI | N-terminus removed |
|---|---|---|---|---|---|---|---|---|---|
| 7 | 31202 | 31201.64 | 31182.25 | 9.10 | 28166 | 28165.90 | 28148.54 | 7.99 | 1-28aa |
| 9 | 30951 | 30951.32 | 30932.03 | 9.09 | 27946 | 27945.57 | 27928.42 | 8.02 | 1-28aa |
| 10 | 31202 | 31201.64 | 31182.25 | 9.10 | 28166 | 28165.90 | 28148.54 | 7.99 | 1-28aa |
| 12 | 31159 | 31158.61 | 31139.26 | 9.25 | 28153 | 28152.90 | 28135.55 | 8.63 | 1-28aa |
| 13 | 31127 | 31126.57 | 31107.10 | 9.07 | 28089 | 28088.76 | 28071.52 | 8.01 | 1-28aa |
| 14 | 30979 | 30979.38 | 30960.06 | 9.09 | 27974 | 27973.62 | 27959.46 | 8.02 | 1-28aa |
| 15 | 31144 | 31143.60 | 31124.26 | 9.38 | 28108 | 28107.86 | 28090.54 | 8.95 | 1-28aa |
| 16 | 30893 | 30893.29 | 30874.28 | 9.27 | 27888 | 27887.53 | 27870.42 | 8.70 | 1-28aa |
| 17 | 30978 | 30978.43 | 30959.11 | 9.39 | 27973 | 27972.68 | 27955.51 | 9.02 | 1-28aa |
| 19 | 30969 | 30969.34 | 30950.04 | 9.09 | 27964 | 27963.58 | 27946.44 | 8.02 | 1-28aa |
| 20 | 31412 | 31411.81 | 31392.21 | 8.91 | 28321 | 28321.04 | 28303.61 | 7.99 | 1-28aa |
| 21 | 30897 | 30897.17 | 30877.98 | 9.21 | 27932 | 27931.54 | 27914.41 | 8.02 | 1-28aa |
| 22 | 31201 | 31200.65 | 31181.28 | 9.38 | 28165 | 28164.91 | 28147.57 | 8.95 | 1-28aa |
| 23 | 31233 | 31232.70 | 31213.30 | 9.38 | 28197 | 28196.96 | 28179.59 | 8.95 | 1-28aa |
| 24 | 31048 | 31048.48 | 31029.13 | 9.27 | 28044 | 28043.73 | 28025.53 | 8.70 | 1-28aa |
| 27 | 30921 | 30921.34 | 30902.06 | 9.27 | 27916 | 27915.59 | 27898.45 | 8.70 | 1-28aa |
| 28 | 31143 | 31142.62 | 31123.27 | 9.49 | 28107 | 28106.88 | 28089.56 | 9.16 | 1-28aa |
| 29 | 31114 | 31113.58 | 31094.25 | 9.38 | 28108 | 28107.86 | 28090.54 | 8.95 | 1-28aa |
| 30 | 31173 | 31172.60 | 31153.24 | 9.10 | 28167 | 28166.88 | 28149.53 | 7.99 | 1-28aa |
| 31 | 31364 | 31363.76 | 31344.21 | 8.91 | 28273 | 28272.99 | 28255.61 | 7.99 | 1-28aa |
| 32 | 31188 | 31187.66 | 31168.28 | 9.38 | 28152 | 28151.92 | 28134.57 | 8.95 | 1-28aa |
| 33 | 31117 | 31116.58 | 31097.25 | 9.28 | 28081 | 28080.84 | 28063.53 | 8.95 | 1-28aa |
| 34 | 31248 | 31247.72 | 31228.24 | 9.00 | 28212 | 28211.98 | 28194.53 | 7.91 | 1-28aa |
| 35 | 31368 | 31367.75 | 31348.21 | 8.91 | 28277 | 28276.98 | 28259.60 | 7.99 | 1-28aa |
| 36 | 31218 | 31217.64 | 31198.26 | 9.25 | 28182 | 28181.90 | 28164.54 | 8.63 | 1-28aa |
| 37 | 31149 | 31148.53 | 31129.20 | 8.90 | 28139 | 28138.83 | 28121.49 | 6.95 | 1-28aa |
| 38 | 31048 | 31048.48 | 31029.13 | 9.27 | 28043 | 28042.73 | 28025.53 | 8.70 | 1-28aa |
| 40 | 31065 | 31065.43 | 31046.01 | 8.45 | 27819 | 27819.40 | 27802.30 | 5.97 | 1-28aa |
| 41 | 31046 | 31045.52 | 31025.98 | 8.96 | 27810 | 27810.46 | 27793.28 | 6.95 | 1-28aa |
| 42 | 31206 | 31205.63 | 31186.26 | 9.25 | 28170 | 28169.89 | 28152.54 | 8.63 | 1-28aa |
| 43 | 31389 | 31388.86 | 31369.29 | 9.27 | 28298 | 28298.09 | 28280.69 | 8.91 | 1-28aa |
| 44 | 31447 | 31446.90 | 31427.30 | 9.12 | 28356 | 28356.13 | 28338.69 | 8.60 | 1-28aa |
| 46 | 31032 | 31032.44 | 31013.09 | 9.09 | 28027 | 28026.69 | 28009.48 | 8.02 | 1-28aa |
| 47 | 31079 | 31078.51 | 31059.14 | 9.27 | 28073 | 28072.76 | 28055.54 | 8.70 | 1-28aa |
| 48 | 31006 | 31006.40 | 30987.07 | 9.09 | 28001 | 28000.65 | 27983.47 | 8.02 | 1-28aa |
| 49 | 31105 | 31104.55 | 31085.16 | 9.27 | 28099 | 28098.80 | 28081.55 | 8.70 | 1-28aa |
| 50 | 31005 | 31005.41 | 30986.08 | 9.09 | 28000 | 27999.66 | 27982.47 | 8.02 | 1-28aa |
| 51 | 30979 | 30979.38 | 30960.06 | 9.09 | 27974 | 27973.62 | 27956.46 | 8.02 | 1-28aa |
| 52 | 31220 | 31219.65 | 31200.27 | 9.25 | 28184 | 28183.91 | 28166.56 | 8.63 | 1-28aa |
| 53 | 31184 | 31183.71 | 31164.31 | 9.25 | 28148 | 28147.97 | 28130.60 | 8.63 | 1-28aa |
| 54 | 31233 | 31232.65 | 31213.27 | 9.25 | 28197 | 28196.91 | 28179.56 | 8.63 | 1-28aa |
| 55 | 31172 | 31171.66 | 31152.29 | 9.38 | 28136 | 28135.92 | 28118.58 | 8.95 | 1-28aa |
| 56 | 31405 | 31404.81 | 31385.24 | 8.91 | 28314 | 28314.05 | 28296.63 | 7.99 | 1-28aa |
| 58 | 31250 | 31249.68 | 31230.28 | 9.25 | 28214 | 28213.94 | 28196.57 | 8.63 | 1-28aa |
| 59 | 31354 | 31353.81 | 31334.25 | 8.91 | 28263 | 28263.04 | 28245.65 | 7.99 | 1-28aa |
| 60 | 31187 | 31186.67 | 31167.29 | 9.25 | 28181 | 28180.95 | 28163.59 | 8.63 | 1-28aa |
| 61 | 31247 | 31246.68 | 31227.27 | 9.10 | 28211 | 28210.94 | 28193.56 | 7.99 | 1-28aa |
| 62 | 31192 | 31191.60 | 31172.24 | 9.25 | 28156 | 28155.86 | 28138.53 | 8.63 | 1-28aa |
| 63 | 31092 | 31092.46 | 31073.02 | 8.45 | 28046 | 28045.63 | 28028.41 | 5.97 | 1-28aa |
| 64 | 31117 | 31116.61 | 31097.31 | 9.30 | 28081 | 28080.86 | 28063.60 | 8.66 | 1-28aa |
| 65 | 31077 | 31076.54 | 31057.16 | 9.27 | 28071 | 28070.79 | 28053.56 | 8.70 | 1-28aa |
| 66 | 31229 | 31228.67 | 31209.27 | 9.25 | 28166 | 28165.90 | 28148.55 | 8.63 | 1-28aa |
| 67 | 30952 | 30952.35 | 30933.05 | 9.09 | 27947 | 27946.60 | 27929.45 | 8.02 | 1-28aa |
| 68 | 31190 | 31189.63 | 31170.27 | 9.27 | 28180 | 28179.93 | 28162.57 | 8.63 | 1-28aa |
| 69 | 31157 | 31156.60 | 31137.25 | 9.40 | 28121 | 28120.86 | 28103.54 | 8.97 | 1-28aa |
| 71 | 31190 | 31189.69 | 31170.24 | 9.30 | 28154 | 28153.95 | 28136.53 | 8.84 | 1-28aa |
| 72 | 31103 | 31102.50 | 31083.18 | 9.10 | 28067 | 28066.76 | 28049.47 | 7.99 | 1-28aa |
| 73 | 31011 | 31011.44 | 30992.03 | 9.09 | 28006 | 28005.68 | 27988.43 | 8.02 | 1-28aa |
| 74 | 31382 | 31381.78 | 31362.22 | 8.91 | 28291 | 28291.01 | 28273.62 | 7.99 | 1-28aa |
| 75 | 31368 | 31367.75 | 31348.21 | 8.91 | 28287 | 28287.02 | 28269.62 | 7.99 | 1-28aa |
| 76 | 31352 | 31351.71 | 31332.18 | 8.91 | 28261 | 28260.94 | 28243.57 | 7.99 | 1-28aa |
| 77 | 31398 | 31397.86 | 31378.29 | 9.25 | 28307 | 28307.09 | 28289.69 | 8.89 | 1-28aa |
| 79 | 31171 | 31170.67 | 31151.30 | 9.49 | 28135 | 28134.93 | 28117.59 | 9.16 | 1-28aa |
| 80 | 31230 | 31229.69 | 31210.29 | 9.25 | 28194 | 28193.95 | 28176.58 | 8.63 | 1-28aa |
| 81 | 31003 | 31003.31 | 30983.99 | 7.77 | 27998 | 27997.56 | 27980.38 | 5.97 | 1-28aa |
| 82 | 31170 | 31169.64 | 31150.27 | 9.38 | 28134 | 28133.90 | 28116.56 | 8.95 | 1-28aa |
| 83 | 30988 | 30988.39 | 30969.06 | 9.09 | 27983 | 27982.63 | 27965.46 | 8.03 | 1-28aa |
| 84 | 30949 | 30949.35 | 30930.05 | 9.09 | 27944 | 27943.60 | 27926.45 | 8.02 | 1-28aa |
| 85 | 30963 | 30963.33 | 30944.03 | 9.09 | 27958 | 27957.58 | 27940.42 | 8.02 | 1-28aa |
| 86 | 31013 | 31013.39 | 30994.05 | 9.09 | 28008 | 28007.64 | 27990.44 | 8.02 | 1-28aa |
| 87 | 31023 | 31023.47 | 31004.12 | 9.09 | 28018 | 28017.72 | 28000.52 | 8.02 | 1-28aa |
| 88 | 31125 | 31124.56 | 31105.21 | 9.25 | 28089 | 28088.82 | 28071.50 | 8.63 | 1-28aa |

TABLE 2-continued

Mass data of CTX-M protein

| | Full-length CTX-M protein | | | | Active protein | | | | |
|---|---|---|---|---|---|---|---|---|---|
| CTX-M | Da | Average molecular weight | Monoisotopic mass | PI | Da | Average molecular weight | Monoisotopic mass | PI | N-terminus removed |
| 90 | 31007 | 31007.43 | 30988.09 | 9.09 | 28002 | 28001.68 | 27984.49 | 8.02 | 1-28aa |
| 92 | 31408 | 31407.82 | 31388.24 | 8.91 | 28317 | 28317.05 | 28299.63 | 7.99 | 1-28aa |
| 93 | 30936 | 30936.31 | 30917.03 | 9.27 | 27931 | 27930.56 | 27913.43 | 8.70 | 1-28aa |
| 95 | 31380 | 31379.76 | 31360.20 | 8.58 | 28289 | 28288.99 | 28271.59 | 7.15 | 1-28aa |
| 96 | 31101 | 31100.58 | 31081.25 | 9.38 | 28095 | 28094.86 | 28077.55 | 8.95 | 1-28aa |
| 97 | 31279 | 31278.65 | 31259.15 | 8.58 | 28287 | 28287.02 | 28269.62 | 7.99 | 1-28aa |
| 98 | 30949 | 30949.39 | 30930.09 | 9.27 | 27944 | 27943.64 | 27926.48 | 8.70 | 1-28aa |
| 99 | 31038 | 31038.45 | 31019.11 | 9.27 | 28033 | 28032.69 | 28015.50 | 8.70 | 1-28aa |
| 100 | 31033 | 31033.47 | 31013.94 | 8.96 | 27798 | 27798.40 | 27781.25 | 6.95 | 1-28aa |
| 101 | 31170 | 31169.68 | 31150.31 | 9.38 | 28134 | 28133.94 | 28116.60 | 8.95 | 1-28aa |
| 102 | 30979 | 30979.38 | 30960.06 | 9.09 | 27974 | 27973.62 | 27956.46 | 8.02 | 1-28aa |
| 103 | 31171 | 31170.63 | 31151.27 | 9.38 | 28135 | 28134.89 | 28117.55 | 8.95 | 1-28aa |
| 104 | 31006 | 31006.40 | 30987.07 | 9.09 | 28001 | 28000.65 | 27983.47 | 8.02 | 1-28aa |
| 105 | 31007 | 31007.43 | 30988.09 | 9.09 | 28002 | 28001.68 | 27984.49 | 8.02 | 1-28aa |
| 110 | 31094 | 31094.42 | 31075.05 | 8.53 | 28089 | 28088.67 | 28071.45 | 6.20 | 1-28aa |
| 111 | 31010 | 31010.39 | 30991.07 | 9.09 | 28005 | 28004.64 | 27987.46 | 8.02 | 1-28aa |
| 112 | 30949 | 30949.35 | 30930.05 | 9.09 | 27944 | 27943.60 | 27926.45 | 8.02 | 1-28aa |
| 113 | 31007 | 31007.43 | 30988.10 | 9.27 | 28002 | 28001.68 | 27984.50 | 8.70 | 1-28aa |
| 114 | 31144 | 31143.60 | 31124.26 | 9.38 | 28108 | 28107.86 | 28090.54 | 8.95 | 1-28aa |
| 115 | 31408 | 31407.82 | 31388.24 | 8.91 | 28317 | 28317.05 | 28299.63 | 7.99 | 1-28aa |
| 116 | 31229 | 31228.71 | 31209.31 | 9.38 | 28193 | 28192.97 | 28175.60 | 8.95 | 1-28aa |
| 117 | 31175 | 31174.62 | 31155.26 | 9.38 | 28139 | 28138.88 | 28121.55 | 8.95 | 1-28aa |
| 121 | 30951 | 30951.37 | 30932.07 | 9.27 | 27946 | 27945.61 | 27928.46 | 8.70 | 1-28aa |
| 122 | 31064 | 31064.48 | 31045.12 | 9.27 | 28059 | 28058.73 | 28041.52 | 8.70 | 1-28aa |
| 123 | 31157 | 31156.58 | 31137.31 | 9.40 | 28121 | 28120.84 | 28103.59 | 8.97 | 1-28aa |
| 124 | 31378 | 31377.79 | 31358.23 | 8.91 | 28287 | 28287.02 | 28269.62 | 7.99 | 1-28aa |
| 125 | 31029 | 31029.44 | 31010.09 | 9.09 | 28024 | 28023.69 | 28006.48 | 8.03 | 1-28aa |
| 126 | 30953 | 30953.34 | 30934.05 | 9.09 | 27948 | 27947.59 | 27930.44 | 8.02 | 1-28aa |
| 127 | 31145 | 31144.59 | 31125.24 | 9.25 | 28109 | 20108.85 | 28091.53 | 8.63 | 1-28aa |
| 129 | 30949 | 30949.35 | 30930.06 | 9.30 | 27944 | 27943.60 | 27926.46 | 8.72 | 1-28aa |
| 130 | 31029 | 31029.44 | 31010.09 | 9.09 | 28024 | 28023.69 | 28006.48 | 8.03 | 1-28aa |
| 131 | 31320 | 31319.75 | 31300.22 | 9.12 | 28229 | 28228.98 | 28211.62 | 8.60 | 1-28aa |
| 132 | 31078 | 31077.54 | 31058.23 | 9.38 | 28042 | 28041.80 | 28024.52 | 8.95 | 1-28aa |
| 132 | 30951 | 30951.37 | 30932.07 | 9.27 | 27946 | 27945.61 | 27928.46 | 8.70 | 1-28aa |
| 136 | 31230 | 31229.69 | 31210.29 | 9.25 | 28194 | 28193.95 | 28176.58 | 8.63 | 1-28aa |
| 137 | 30857 | 30857.39 | 30838.05 | 9.32 | 27852 | 27851.64 | 27834.44 | 8.95 | 1-28aa |
| 138 | 31220 | 31219.61 | 31200.24 | 9.25 | 28184 | 28183.87 | 28166.52 | 8.63 | 1-28aa |
| 139 | 31128 | 31127.60 | 31108.26 | 9.40 | 28108 | 28107.86 | 28090.54 | 8.95 | 1-28aa |
| 141 | 31436 | 31435.83 | 31416.24 | 8.58 | 28345 | 28345.06 | 28327.63 | 7.15 | 1-28aa |
| 142 | 31143 | 31142.62 | 31123.27 | 9.49 | 28107 | 28106.88 | 28089.56 | 9.16 | 1-28aa |
| 144 | 31188 | 31187.70 | 31168.32 | 9.38 | 28152 | 28151.96 | 28134.61 | 8.95 | 1-28aa |
| 146 | 31274 | 31273.71 | 31254.29 | 9.27 | 28238 | 28237.97 | 28220.58 | 8.64 | 1-28aa |
| 147 | 30997 | 30997.39 | 30978.07 | 9.09 | 27992 | 27991.64 | 27974.47 | 8.02 | 1-28aa |
| 148 | 31059 | 31058.51 | 31039.20 | 9.27 | 28053 | 28052.75 | 28035.60 | 8.70 | 1-28aa |
| 150 | 31203 | 31202.68 | 31183.28 | 9.38 | 28167 | 28166.94 | 28149.57 | 8.95 | 1-28aa |
| 155 | 31072 | 31071.54 | 31052.24 | 9.49 | 28036 | 28035.80 | 28018.52 | 9.16 | 1-28aa |
| 156 | 31130 | 31129.53 | 31110.20 | 9.27 | 28094 | 28093.79 | 28076.49 | 8.64 | 1-28aa |
| 157 | 31086 | 31085.57 | 31066.25 | 9.49 | 28050 | 28049.83 | 28032.54 | 9.16 | 1-28aa |
| 158 | 31274 | 31273.75 | 31254.32 | 9.25 | 28238 | 28238.01 | 28220.61 | 8.63 | 1-28aa |
| 159 | 30920 | 30920.40 | 30901.11 | 9.51 | 27915 | 27914.64 | 27897.50 | 9.24 | 1-28aa |
| 161 | 31051 | 31051.44 | 31032.08 | 8.86 | 28046 | 28045.69 | 28028.48 | 6.96 | 1-28aa |
| 162 | 31133 | 31132.53 | 3113.19 | 9.10 | 28166 | 28165.90 | 28148.55 | 8.63 | 1-28aa |
| 163 | 31074 | 31074.49 | 31055.19 | 9.25 | 28108 | 28107.86 | 28090.54 | 8.95 | 1-28aa |
| 164 | 31172 | 31171.70 | 31152.32 | 9.47 | 28136 | 28135.92 | 28118.58 | 8.95 | 1-28aa |
| 165 | 31351 | 31350.76 | 31331.22 | 8.91 | 28260 | 28259.99 | 28242.61 | 7.99 | 1-28aa |
| 166 | 31274 | 31273.75 | 31254.32 | 9.25 | 28238 | 28238.01 | 28220.61 | 8.63 | 1-28aa |
| 167 | 31248 | 31247.73 | 31228.25 | 9.16 | 28212 | 28211.99 | 28194.54 | 8.51 | 1-28aa |
| 168 | 31019 | 31019.40 | 31000.07 | 9.09 | 28014 | 28013.65 | 27996.46 | 8.03 | 1-28aa |
| 169 | 31117 | 31116.58 | 31097.25 | 9.38 | 28081 | 28080.84 | 28063.53 | 8.95 | 1-28aa |
| 170 | 31143 | 31142.62 | 31123.27 | 9.49 | 28107 | 28106.88 | 28089.56 | 9.16 | 1-28aa |
| 171 | 31309 | 31308.68 | 31289.16 | 8.58 | 28218 | 28217.91 | 28200.55 | 7.15 | 1-28aa |
| 172 | 31128 | 31127.56 | 31108.22 | 9.38 | 28092 | 28091.82 | 28074.51 | 8.95 | 1-28aa |
| 173 | 31174 | 31173.63 | 31154.27 | 9.38 | 28138 | 28137.89 | 28120.55 | 8.95 | 1-28aa |
| 174 | 30906 | 30906.37 | 30887.08 | 9.27 | 27916 | 27915.59 | 27898.45 | 8.70 | 1-28aa |
| 175 | 31276 | 31275.72 | 31256.30 | 9.25 | 28240 | 28239.98 | 28222.59 | 8.63 | 1-28aa |
| 176 | 31114 | 31113.58 | 31094.25 | 9.38 | 28078 | 28077.84 | 28060.53 | 8.95 | 1-28aa |
| 177 | 31187 | 31186.67 | 31167.29 | 9.25 | 28151 | 28150.93 | 28133.57 | 8.63 | 1-28aa |
| 178 | 31174 | 31173.63 | 31154.27 | 9.38 | 28138 | 28137.89 | 28120.55 | 8.95 | 1-28aa |
| 179 | 31176 | 31175.65 | 31156.28 | 9.38 | 28140 | 28139.90 | 28122.57 | 8.95 | 1-28aa |
| 180 | 31174 | 31173.63 | 31154.27 | 9.38 | 28138 | 28137.89 | 28120.55 | 8.95 | 1-28aa |
| 181 | 31167 | 31166.64 | 31147.27 | 9.38 | 28131 | 28130.90 | 28113.56 | 8.95 | 1-28aa |
| 182 | 31172 | 31171.62 | 31152.26 | 9.40 | 28136 | 28135.88 | 28118.55 | 8.97 | 1-28aa |

TABLE 2-continued

Mass data of CTX-M protein

| | Full-length CTX-M protein | | | | Active protein | | | | |
|---|---|---|---|---|---|---|---|---|---|
| CTX-M | Da | Average molecular weight | Monoisotopic mass | PI | Da | Average molecular weight | Monoisotopic mass | PI | N-terminus removed |
| 183 | 31171 | 31170.67 | 31151.30 | 9.47 | 28135 | 28134.93 | 28117.59 | 9.14 | 1-28aa |
| 184 | 31131 | 31130.60 | 31111.26 | 9.38 | 28095 | 28094.86 | 28077.55 | 8.95 | 1-28aa |
| 186 | 31118 | 31117.52 | 31098.20 | 9.38 | 28108 | 28107.86 | 28090.54 | 8.95 | 1-28aa |
| 187 | 31206 | 31205.58 | 31186.22 | 9.25 | 28170 | 28169.84 | 28152.51 | 8.63 | 1-28aa |
| 188 | 31174 | 31173.63 | 31154.27 | 9.38 | 28138 | 28137.89 | 28120.55 | 8.95 | 1-28aa |
| 189 | 31114 | 31113.58 | 31094.25 | 9.38 | 28078 | 28077.84 | 28060.53 | 8.95 | 1-28aa |
| 190 | 31186 | 31185.68 | 31166.30 | 9.38 | 28150 | 28149.94 | 28132.59 | 8.95 | 1-28aa |
| 191 | 30980 | 30980.36 | 30961.04 | 8.86 | 27975 | 27974.61 | 27957.44 | 6.95 | 1-28aa |
| 192 | 30949 | 30949.35 | 30930.06 | 9.30 | 27944 | 27943.60 | 27926.46 | 8.72 | 1-28aa |
| 193 | 31174 | 31173.63 | 31154.27 | 9.38 | 28138 | 28137.89 | 28120.55 | 8.95 | 1-28aa |
| 194 | 31125 | 31124.56 | 31105.21 | 9.25 | 28108 | 28107.86 | 28090.54 | 8.95 | 1-28aa |
| 195 | 30894 | 30894.31 | 30875.04 | 9.27 | 27889 | 27888.56 | 27871.44 | 8.70 | 1-28aa |
| 196 | 30990 | 30990.45 | 30971.12 | 9.42 | 27985 | 27984.70 | 27967.52 | 9.04 | 1-28aa |
| 197 | 31130 | 31129.58 | 31110.24 | 9.38 | 28094 | 28093.84 | 28076.53 | 8.95 | 1-28aa |
| 198 | 30953 | 30953.34 | 30934.05 | 9.09 | 27974 | 27973.62 | 27956.46 | 8.02 | 1-28aa |
| 199 | 31161 | 31160.66 | 31141.34 | 9.30 | 28125 | 28124.92 | 28107.63 | 8.66 | 1-28aa |
| 200 | 31404 | 31403.87 | 31384.28 | 8.91 | 28313 | 28313.10 | 28295.68 | 7.99 | 1-28aa |
| 201 | 31208 | 31028.45 | 31009.08 | 9.07 | 28023 | 28022.70 | 28005.48 | 8.01 | 1-28aa |
| 202 | 31156 | 31155.66 | 31136.29 | 9.38 | 28120 | 28119.92 | 28102.58 | 8.95 | 1-28aa |
| 203 | 31230 | 31229.65 | 31210.27 | 9.27 | 28194 | 28193.91 | 28176.56 | 8.64 | 1-28aa |
| 204 | 31214 | 31213.69 | 31194.30 | 9.25 | 28178 | 28177.95 | 28160.59 | 8.63 | 1-28aa |
| 206 | 31175 | 31174.61 | 31155.25 | 9.25 | 28139 | 28138.87 | 28121.54 | 8.63 | 1-28aa |
| 207 | 31202 | 31201.68 | 31182.30 | 9.38 | 28166 | 28165.94 | 28148.59 | 8.95 | 1-28aa |
| 208 | 31202 | 31201.64 | 31182.26 | 9.25 | 28166 | 28165.90 | 28148.55 | 8.63 | 1-28aa |
| 209 | 31156 | 31155.66 | 31136.29 | 9.38 | 28120 | 28119.92 | 28102.58 | 8.95 | 1-28aa |
| 210 | 31174 | 31173.63 | 31154.27 | 9.38 | 28138 | 28137.89 | 28120.55 | 8.95 | 1-28aa |
| 212 | 31234 | 31233.68 | 31214.29 | 9.25 | 28198 | 28197.94 | 28180.58 | 8.63 | 1-28aa |
| 213 | 31128 | 31127.51 | 31108.04 | 8.51 | 28090 | 28089.70 | 28072.47 | 6.21 | 1-28aa |
| 214 | 30981 | 30981.35 | 30962.04 | 9.09 | 27976 | 27975.60 | 27958.44 | 8.02 | 1-28aa |
| 215 | 31030 | 31030.42 | 31011.07 | 8.86 | 28025 | 28024.67 | 28007.47 | 7.04 | 1-28aa |
| 216 | 31174 | 31173.63 | 31154.27 | 9.38 | 28138 | 28137.89 | 28120.55 | 8.95 | 1-28aa |
| 218 | 31158 | 31157.63 | 31138.27 | 9.38 | 28122 | 28121.89 | 28104.56 | 8.95 | 1-28aa |
| 219 | 30981 | 30981.39 | 30962.08 | 9.09 | 27976 | 27975.64 | 27958.47 | 8.02 | 1-28aa |
| 220 | 31175 | 31174.61 | 31155.25 | 9.25 | 28139 | 28138.87 | 28121.54 | 8.63 | 1-28aa |
| 221 | 30905 | 30905.39 | 30886.03 | 9.18 | 27900 | 27899.64 | 27882.43 | 8.63 | 1-28aa |
| 222 | 31260 | 31259.72 | 31240.30 | 9.25 | 28224 | 28223.98 | 28206.59 | 8.63 | 1-28aa |
| 223 | 30922 | 30922.37 | 30903.08 | 9.27 | 27917 | 27916.61 | 27899.47 | 8.70 | 1-28aa |
| 224 | 31015 | 31015.47 | 30996.20 | 9.38 | 28108 | 28107.86 | 28090.54 | 8.95 | 1-28aa |
| 225 | 31174 | 31173.63 | 31154.27 | 9.38 | 28138 | 28137.89 | 28120.55 | 8.95 | 1-28aa |
| 226 | 31176 | 31175.65 | 31156.28 | 9.38 | 28136 | 28135.92 | 28118.58 | 8.95 | 1-28aa |

Although the present invention has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereto.

The invention claimed is:

1. A method of detecting a pathogenic strain having resistance to β-lactam antibiotics in a biological sample, comprising:

(a) isolating a protein expressed by a pathogenic strain in a biological sample isolated from a subject by lysing cells of the pathogenic strain by applying osmotic pressure to the biological sample using a hypertonic NaCl solution; and (b) performing matrix-assisted laser desorption/ionization time of flight (MALDI-TOF) mass spectrometry on the isolated protein, wherein the isolated protein is subjected to MALDI-TOF mass spectrometry without desalting or purification for removing NaCl, wherein it is determined that the pathogenic strain having resistance to β-lactam antibiotics is present in the biological sample when a mass value is detected by the mass spectrometry that has a same value as a mass of a β-lactamase from which 28 amino acid residues at the N-terminus thereof have been removed, wherein the pathogenic strain having resistance to β-lactam antibiotics expresses a CTX-M protein selected from the group consisting of CTX-M1, CTX-M14, CTX-M17, CTX-M24, CTX-M27, CTX-M28, CTX-M32, CTX-M55, CTX-M79, CTX-M98, CTX-M113, CTX-M123, CTX-M129, CTX-M142 and CTX-M186, and wherein the β-lactamase is a CTX-M protein selected from the group consisting of CTX-M1, CTX-M14, CTX-M17, CTX-M24, CTX-M27, CTX-M28, CTX-M32, CTX-M55, CTX-M79, CTX-M98, CTX-M113, CTX-M123, CTX-M129, CTX-142 and CTX-M186.

2. The method of claim 1, further comprising performing ion exchange chromatography on the protein isolated in step (a).

3. The method of claim 2, wherein the ion exchange chromatography is anion exchange chromatography.

4. The method of claim 1, wherein it is determined that the pathogenic strain having resistance to beta-lactam antibiotics is present in the biological sample, when one or more mass values (m/z×z) selected from the group consisting of 28210, 27974, 28108, 27973, 28044, 27916, 28107, 28136, 28121, 28135, 27944, and 28002 are detected as a result of the mass spectrometry, wherein 28210 corresponds to mass value (m/z×z) of CTX-M1,
27974 corresponds to mass value (m/z×z) of CTX-M14,
27973 corresponds to mass value (m/z×z) of CTX-M17,
28044 corresponds to mass value (m/z×z) of CTX-M24,
27916 corresponds to mass value (m/z×z) of CTX-M27,
28107 corresponds to mass value (m/z×z) of CTX-M28 or CTX-M142,
28152 corresponds to mass value (m/z×z) of CTX-M32,
28136 corresponds to mass value (m/z×z) of CTX-M55,
28135 corresponds to mass value (m/z×z) of CTX-M79,
27944 corresponds to mass value (m/z×z) of CTX-M98 or CTX-M129,
28002 corresponds to mass value (m/z×z) of CTX-M113,
28121 corresponds to mass value (m/z×z) of CTX-M123, and
28108 corresponds to mass value (m/z×z) of CTX-M186.

* * * * *